(12) United States Patent
Contag et al.

(10) Patent No.: US 7,449,615 B2
(45) Date of Patent: Nov. 11, 2008

(54) NON-INVASIVE EVALUATION OF PHYSIOLOGICAL RESPONSE IN A TRANSGENIC MOUSE

(75) Inventors: Pamela R. Contag, San Jose, CA (US); Ning Zhang, Alameda, CA (US)

(73) Assignee: Xenogen Corporation, Alameda, CA (US)

( * ) Notice: Subject to any disclaimer, the term of this patent is extended or adjusted under 35 U.S.C. 154(b) by 219 days.

(21) Appl. No.: 09/464,795

(22) Filed: Dec. 16, 1999

(65) Prior Publication Data

US 2002/0138855 A1    Sep. 26, 2002

Related U.S. Application Data

(60) Provisional application No. 60/112,646, filed on Dec. 17, 1998, provisional application No. 60/152,853, filed on Sep. 8, 1999.

(51) Int. Cl.
*A01K 67/027* (2006.01)
*G01N 33/00* (2006.01)

(52) U.S. Cl. .......................................... 800/3; 800/18
(58) Field of Classification Search ................. 800/3, 800/8, 13, 18, 21, 14
See application file for complete search history.

(56) References Cited

U.S. PATENT DOCUMENTS

| 5,650,135 A * | 7/1997 | Contag et al. ................. 424/9.1 |
| 6,020,121 A | 2/2000 | Bao et al. ........................ 435/4 |
| 6,217,847 B1 | 4/2001 | Contag et al. ................. 424/9.4 |

FOREIGN PATENT DOCUMENTS

| EP | 0123456 A2 * | 1/2000 |
| WO | WO 93/23533 A | 11/1993 |
| WO | WO 96/40979 A1 | 12/1996 |
| WO | WO 97/11690 A2 | 4/1997 |
| WO | WO 97/11690 A3 | 4/1997 |
| WO | WO 97/18841 | 5/1997 |
| WO | WO 97/40381 A1 | 10/1997 |
| WO | WO 98/28971 A | 7/1998 |
| WO | WO 98/36081 A | 8/1998 |
| WO | WO 99/11772 | 3/1999 |
| WO | WO 99/11772 A | 3/1999 |
| WO | WO 99/37142 A | 7/1999 |
| WO | WO 00/36106 | 6/2000 |
| WO | WO 00/54581 A2 | 9/2000 |
| WO | WO 00/54581 A3 | 9/2000 |
| WO | WO 01/18195 A2 | 3/2001 |
| WO | WO 01/18225 A1 | 3/2001 |
| WO | WO 01/37195 A2 | 5/2001 |

OTHER PUBLICATIONS

C. Cui et al., Transgenic Research, "Reporter genes in transgenic mice," Review, 1994, 3, pp. 182-194.*
R. E. Hammer et al., Cell Press, "Spontaneous Inflammatory disease in transgenic rats expressing HLA-B27 and Human beta2m: An animal model of HLA-B27-associated human disorders," Nov. 1990, vol. 63,pp. 1099-1112.*
J. J. Mullins et al., Hypertension, "Transgenesis in Nonmurine Species," 1993, 22, pp. 630-633.*
E.R. Cameron, "Recent Advances in Transgenic Technology," Molecular Biotechnology, 1997, vol. 7, pp. 253-265.*
A.L. Boyd et al., "Review: Molecular Biology of Transgenic Animals," J.Anim. Sci. 1993, 71(Suppl.3), 1-9.*
Shibahara et al. Eur J Bichem 179 :557-563, 1989, abstract only.*
Wood (Comparative Medicine 50 (1): 12-15, 2000.*
Contag et al. Journal of Perinatology 21:S119-S124, 2001.*
JAX Mice Price List, Jun. 1997, p. 19 (The Jackson Laboratory, Bar Harbor, Maine).*
Mayerhofer et al., "Monitoring of Spatial Expression of Firefly Luciferase in Transformed Zebrafish," *J Biolumin Chemilumin* 10:271-275, 1995.
Zhang et al., "Bioluminescence For Biological Sensing in Living Mammals," *Adv. Exper. Med. Biol.* 471:775-784, 1999.
Contag et al., "Visualizing Gene Expression in Living Mammanls Using a Bioluminescent Reporter," *Photochemistry and Photobiology* 66(4):523-531, 1997.

* cited by examiner

*Primary Examiner*—Anne-Marie Falk
(74) *Attorney, Agent, or Firm*—Robins & Pasternak LLP

(57) ABSTRACT

The present invention relates to panels of reporter expression cassettes and the generation of transgenic non-human animals, wherein said reporter expression cassettes have selected control elements operable linked to reporter genes. The invention includes methods of use thereof for the identification and characterization of the effects of compounds administered to the live transgenic non-human animals.

10 Claims, 1 Drawing Sheet

NON-INVASIVE EVALUATION OF PHYSIOLOGICAL RESPONSE IN A TRANSGENIC MOUSE

CROSS REFERENCE TO RELATED APPLICATIONS

This application is related to U.S. Provisional Patent Applications Ser. Nos. 60/112,646, and 60/152,853 filed Dec. 17, 1998, and Sep. 8, 1999, respectively, from which priority is claimed under 35 USC §119(e) (1), and which applications are incorporated herein by reference in their entireties.

TECHNICAL FIELD

The present invention relates to diagnostic mammalian models, test animals, methods of creating such animals, and methods of use thereof for the identification and characterization of compounds.

BACKGROUND OF THE INVENTION

Toxicology studies of substances have traditionally relied on unicellular (for example, the Ames test or the yeast carcinogenic assay described in U.S. Pat. No. 4,997,757) or in vitro systems for toxicity testing and the prediction of human risk. However, there are many factors that make it difficult to extrapolate from such data to human risk including cellular affinity of the substance, uptake and distribution differences between single cells and whole animals, metabolism of the substance, and cascade effects where the effect of the substance is mediated through a cellular process. These same factors can affect the progress of pharmaceutical research and development as well when attempting to determining and/or predicting the effects of a compound in an animal system.

Further, the end-point of traditional animal based toxicology studies is typically determination of an LD50 (the dose at which 50% of the test animals die). Dead animals may be subjected to further analysis, for example, histopathology, but such analysis is generally labor intensive and relatively insensitive.

MacGregor, et al (*Fundamental and Applied Toxicology*, 26:156-173, 1995) have reviewed molecular end-points and methods of routine toxicity testing including the following: damage-inducible genes in individual cells; bacterial models of toxicity; screening of stress-gene expression using hybridization or polymerase chain reaction; hybridization probes for detection of chromosomal aberrations; single cell electrophoresis assays; and in vivo animal studies involving animal sacrifice and subsequent analysis of tissue/cellular damage.

General strategies for generating transgenic (Tg) animals has been well described (Pinkert, C. A. (ed.) 1994. Transgenic animal technology: A laboratory handbook. Academic Press, Inc., San Diedo, Calif.; Monastersky G. M. andRobl, J. M. (ed.) (1995) Strategies in transgenic animal science. ASM Press. Washington D.C.), however, the time-consuming processes of screening for presence and function of the transgene remained rate limiting steps. These screens typically involve conventional assays, PCR, Southern blot hybridization or slot-blot hybridization (Tinkle, B. T. et al., (1994) In Pinkert, C. A. ed., Transgenic animal technology: A laboratory handbook, pp. 221-34 Academic Press, Inc., San Diego, Calif.), to demonstrate the presence of integrated DNA. To determine if the gene products are expressed steady-state levels of mRNA transcripts can be assessed by Northern blot hybridization, RT-PCR, or in situ hybridization, and protein expression assayed using Western blots, or immunofluorescent staining. Finally, a wide range of assays are needed to determine function as an indication of the appropriate phenotype. Tissues from the Tg animal are required to perform these molecular and functional analyses (Bieberich, C. J., et al., (1994) In Pinkert, C. A. ed., Transgenic animal technology: A laboratory handbook, pp. 235-62. Academic Press, Inc., San Diego, Calif.), and removal of tissues may not be possible until a line is established. Thus, a rapid noninvasive screening method is needed as a functional assay for the generation and study of Tg animals.

A wide range of Tg mice that employ reporter constructs have been developed and tested. For example, Tg mice containing viral long terminal repeat (LTR) promoter fusions have been used to study the range of tissues and cell types that are capable of supporting HTLV-1 expression and the development of neurofibromatosis-like tumors associated with HTLV-1 retrovirus (Bieberich, C. J., et al., (1993) Virol. 196: 309-18.). The LTR from HIV-1 has been fused to luciferase to evaluate transcriptional regulation by UV light and various sensitizing agents (Morrey, J. D., et al., (1992) J. Acquir. Immune Defic. Syndr. 5: 1195-203; Morrey, J. D., et al., (1991) J Viol. 65: 5045-51). Cardiovascular biology and diseases have been investigated in Tg mouse models using tissue-specific promoters (Johnson, J., et al., (1989) Mol. Cell. Biol. 9: 3393-9; Rindt, H., et al., (1993) J. Biol. Chem. 268: 5332-8; Seidman, C. E., et al., (1991) Can. J. Physiol.Pharmacol. 69: 1486-92; Tsika, R. W., et al., (1990) Proc. Natl. Acad. Sci. USA. 87: 379-83), and regulation of insulin-responsive glucose transporter GLUT4 and Apo A-I genes have also studied in models of diabetes, obesity (Liu, M. L., et al., (1992) J. Biol. Chem. 267: 11673-6) and coronary artery disease (Walsh, A., et al., (1993) J. Lipid Res. 34: 617-23; Walsh, A., et al., (1989) J. Biol. Chem. 264: 6488-94).

Photoproteins as biological labels have been used for more than a decade for the study of gene expression in cell culture or using excised tissues (Campbell, A. K. 1988. Chemiluminescence. Principles and applications in biology and medicine. Ellis Horwood Ltd. and VCH Verlagsgesellschaft mbH, Chichester, England; Hastings, J. W. (1996) Gene. 173:5-11; Morrey, J. D., et al., (1992) J. Acquir. Immune Defic. Syndr. 5: 1195-203; Morrey, J. D., et al., (1991) J Viol. 65: 5045-51.). Low-light imaging of internal bioluminescent signals has been used to study temporal and spatial gene regulation in relatively thin or nearly transparent organisms (Millar A. J., et al., (1992) Plant Cell 4:1075-87; Stanewsky, R., et al., (1997) EMBO J. 16:5006-18; Brandes C, et al., (1996) Neuron 16:687-92). External detection of internal light penetrating the opaque animal tissues has been described (Contag, P. R., et al., (1998) Nature Med. 4:245-7; Contag, C. H., et al., (1997) Photochem Photobiol. 66:523-31; Contag, C. H., et al., (1995) Mol Microbiol. 18:593-603).

However, heretofore no in vivo screening method has been described that allows screening of compounds in whole, live animals where real-time data could be collected concerning the effects of a test substance on, for example, specific aspects of toxicity and substance metabolism.

SUMMARY OF THE INVENTION

The present invention includes expression cassettes, panels of expression cassettes, transgenic non-human animals carrying said expression cassettes, diagnostic transgenic nonhuman animal models, test animals, methods of creating such animals, and methods of using such animals for the identification and characterization of compounds.

In one aspect, the present invention relates to a panel of expression cassettes, comprising a first expression cassette comprising a selected first control element operable linked to sequences encoding a first light generating polypeptide, and a second expression cassette comprising a selected second control element operable linked to sequences encoding a second light generating polypeptide.

Although in a preferred embodiment the control elements are derived from different genes, they may also be derived from the same or similar genes and operably linked to the same or different light generating polypeptides. For example, the same control element may be operably linked to light generating polypeptide encoding sequences derived from a luc gene and a lux gene.

Such panels may include three, four, five or more such expression cassettes, typically not more than 10 and usually not more than 15-50. The light generating polypeptides in these expression cassettes may all be the same or they may be different. The light generating polypeptides can, for example, for derived from coding sequences for lux, luc, or fluorescent proteins (e.g., green fluorescent protein).

The selected control elements of the present invention can be chosen from groups of genes including, but not limited to, the following: stress-inducible genes; apoptosis-related genes; angiogenesis-related genes; inflammation-related genes; genes whose expression is induced in a host in response to an infectious agent; genes from single, branched, or related biochemical pathways; oncogenesis-related genes; and development-related genes.

In one embodiment of the present invention the expression cassettes are assembled into kits, for example, for commercial sale and/or use. Such kits may include the expression cassettes in suitable vector(s) for use to be used in the generation of transgenic, non-human animals.

Another aspect of the present invention includes a transgenic, non-human animal comprising any panel of expression cassettes described herein, wherein the expression cassettes have been introduced into the animal or an ancestor of the animal, at an embryonic stage.

The invention also includes providing the transgenic animals of the invention for use in, for example, methods of evaluating the effects of compounds in living animals. Such effects may include determination of toxocological and pharmacological data.

In yet another aspect, the present invention includes a cohort of transgenic, non-human animals comprising any panel of expression cassettes described herein, wherein (i) each transgenic animal of the cohort contains at least one expression cassette of the panel, and (ii) the transgenic animals comprising the cohort are substantially isogenic relative to each other. Methods of generating substantially isogenic cohorts of animals are described herein (e.g., FIG. 1).

A further aspect of the present invention includes a method of determining the effect of an analyte on gene expression mediated by selected control elements, wherein said expression is in a non-human living animal. In the method an analyte is administered to a living transgenic non-human animal of the present invention. Typically, administration of the analyte is carried out under conditions that permit light generation mediated by the light generating polypeptide in the transgenic animal. The effect of the analyte on expression of the light generating polypeptide in a living animal is determined. The expression of the light generating protein under the control of a selected control element reflects the effect of the compound on expression of, for example, a gene native to the animal where the gene has the same control element. This method may further comprise administration of a suitable substrate for the light generating polypeptide (e.g., luciferin). The invention also includes such a method wherein a cohort of animals is used in the screening of the analyte, wherein the administration of the analyte is to each transgenic animal comprising the cohort.

In yet another aspect the present invention includes a non-invasive method for detecting a level expression in response to an analyte, wherein the expression is (i) mediated by selected control elements, and (ii) in a non-human living animal. In this method, the analyte is administered a living transgenic non-human animal carrying a panel of expression cassettes of the present invention. The analyte is administered under conditions that permit light generation mediated by the light generating polypeptide. The animal is then placed within a detection field of a photo detector device and maintained in the detection field of the device in order to measure photon emission from the animal. The measurement is carried out with the photo detector device to detect the level of expression of the light generating polypeptide in the living animal wherein the expression is mediated by at least one of the control elements. Further, the animal may be maintained in the detection field over a defined time period (e.g., minutes or hours) and the level of photon emission from the animal performed at a selected interval to detect changes in the level of the light emission in the animal over time. As described above, this method may also be performed on individual transgenic non-human animals of a cohort of the present invention.

The transgenic animals described herein are useful for studying in vivo regulation of selected genes. Also described herein are methods of generating populations of substantially isogenic transgenic animals, as well as, vectors useful in these methods.

Accordingly, in one embodiment, the subject invention is directed to a transgenic, non-human mammal, for example, a rodent such as a mouse. The mammal comprises at least one single-copy, non-essential gene in its genome, wherein (i) at least a portion of at least one single-copy, non-essential gene is replaced by polynucleotide sequences heterologous to the gene, and (ii) the polynucleotide sequences comprise a first expression cassette which has been introduced into the mammal or an ancestor of the mammal, at an embryonic stage. The first expression cassette comprises a first selectable marker, a first transcriptional promoter element heterologous to the gene, and light-generating protein coding sequences. The light-generating protein coding sequences are operably linked to the promoter element.

The single-copy, non-essential gene may be selected from the group consisting of vitronectin, fosB, and galactin 3 and the first selectable marker may be selected from the group consisting of neomycin phosphotransferase II, xanthine-guanine phosphoribosyltransferase, hygromycin-B-phosphotransferase, chloramphenicol acetyltransferase, and adenine-phosphoribosyl transferase.

In alternative embodiments, the first transcriptional promoter element is an inducible promoter, a repressible promoter, or a constitutive promoter, and may be selected from the group consisting of VEGF, VEGFR, and TIE2.

In additional embodiments, the transgenic, non-human mammal described above comprises a second single-copy, non-essential gene in its genome, wherein (i) at least a portion of the second single-copy, non-essential gene is replaced by polynucleotide sequences heterologous to the second gene, and (ii) the polynucleotide sequences comprise a second expression cassette which has been introduced into the mammal or an ancestor of the mammal, at an embryonic stage. The second expression cassette comprises a second selectable marker, a second transcriptional promoter element heterologous to the second gene, and light generating protein coding sequences. The light generating protein coding sequences are operably linked to the promoter element. Such animals containing multiple expression cassettes can be generated directly by the methods described herein (i.e., direct integration of reporter expression cassettes at selected site(s)) or by breeding transgenic animals of the present invention where the breeding partners each contain different reporter expression cassettes. When transgenic animals are generating by breeding partners, progeny comprising the desired combinations of reporter expression cassettes are identified by methods known in the art (e.g., identification of selectable markers, Northern analysis, genomic DNA analysis, etc.).

The first and second transcriptional promoter elements and selectable markers may be the same or different and the light generating protein in the first expression cassette can produce a different color of light relative to the light generating protein in the second expression cassette.

In yet a further embodiment, the invention is directed to a method of producing a transgenic, non-human mammal, such as a mouse. The mammal has at least one single-copy, non-essential gene in its genome. The method comprises transfecting an embryonic stem cell of the mammal with a linear vector comprising (a) a first selectable marker and a reporter expression cassette, the reporter expression cassette comprising a transcriptional promoter element operably linked to a light generating protein coding sequence, and (b) targeting polynucleotide sequences homologous to a single-copy, non-essential gene in said mammal's genome, the targeting polynucleotide sequences flanking (a), wherein (i) the length of the polynucleotide sequences are sufficient to facilitate homologous recombination between the vector and the single-copy, non-essential gene, and (ii) the transcriptional promoter element is heterologous to the single-copy, non-essential gene;

selecting embryonic stem cells which each have the first selectable marker and reporter expression cassette integrated into its genome;

injecting the embryonic stem cells into a host embryo, implanting the embryo in a foster mother, maintaining the foster mother under conditions which allow production of an offspring that is a transgenic, non-human mammal carrying the reporter expression cassette.

In certain embodiments, the offspring is capable of germline transmission of the reporter expression cassette and the method may further comprise breeding the offspring with a mammal which is substantially isogenic with the embryonic stem cells, such that the breeding yields transgenic F1 offspring carrying the reporter cassette. In particular embodiments, the method comprises breeding the first F1 offspring carrying the reporter cassette with a second F1 offspring carrying the reporter cassette, wherein the breeding yields transgenic F2 offspring carrying the reporter cassette.

In additional embodiments, the embryonic stems cells may be derived from a mouse having a dark coat color, the mammal substantially isogenic with the embryonic stem cells may have a light coat color, and/or the F2 offspring carrying the reporter cassette may have a light coat color. In particular embodiments, the embryonic stems cells are derived from a C57BL/6 mouse having a dark coat color, and the mammal substantially isogenic with the embryonic stem cells is a C57BL/6-Tyr C2j/+mouse having a light coat color.

Different transgenic F2 offspring generated by this method may be bred with each other to obtain further transgenic, non-human animals carrying multiple expression cassettes (wherein different expression cassettes were carried by different F2 offspring).

In still a further embodiment, the subject invention is directed to a vector for use in generating a transgenic non-human mammal, for example, a rodent such as a mouse. The mammal has at least one single-copy, non-essential gene in its genome. The vector comprises (a) a first selectable marker and a reporter expression cassette, the reporter expression cassette comprising a transcriptional promoter element operably linked to a light generating protein coding sequence, and (b) targeting polynucleotide sequences homologous to a single-copy, non-essential gene in the mammal's genome, the targeting polynucleotide sequences flanking (a), wherein (i) the length of the targeting polynucleotide sequences are sufficient to facilitate homologous recombination between the vector and the single-copy, non-essential gene, and (ii) the transcriptional promoter element is heterologous to the single-copy, non-essential gene.

In certain embodiments, the first selectable marker provides a positive selection and may be selected from the group consisting of neomycin phosphotransferase II, xanthine-guanine phosphoribosyltransferase, hygromycin-B-phosphotransferase, chloramphenicol acetyltransferase, and adenine-phosphoribosyl transferase. Additionally, the transcriptional promoter element may be an inducible promoter, a repressible promoter, or a constitutive promoter, and may be selected from the group consisting of VEGF, VEGFR, and TIE2.

In alternative embodiments, the vector further comprises a second selectable marker and at least one target polynucleotide sequence is located between the second selectable marker and the first selectable marker. Additionally, the second selectable marker may provide a negative selection and may be selected from the group consisting of adenosine deaminase, thymidine kinase, and dihydrofolate reductase.

The vectors described above may be circular and may contain at least one restriction site whose cleavage results in a linear vector having the following arrangement of elements: target polynucleotide sequence—(a)—targeting polynucleotide sequences or target polynucleotide sequence—(a)—targeting polynucleotide sequences B (second selectable marker).

The coding sequences of the reporter expression cassette present in the vector may comprise codons that are optimal for expression in a host system into which the expression cassette is to be introduced. Additionally, the targeting polynucleotide sequences from single-copy, non-essential genes may be selected from the group consisting of vitronectin, fosB, and galactin 3.

The light-generating protein in the mammals and methods described above may be derived from either procaryotic or eucaryotic sources and, in particularly preferred embodiments, the light generating protein is a luciferase.

These and other embodiments of the present invention will be apparent to those of skill in the art in view of the teachings herein.

DETAILED DESCRIPTION OF THE INVENTION

Figure 1:
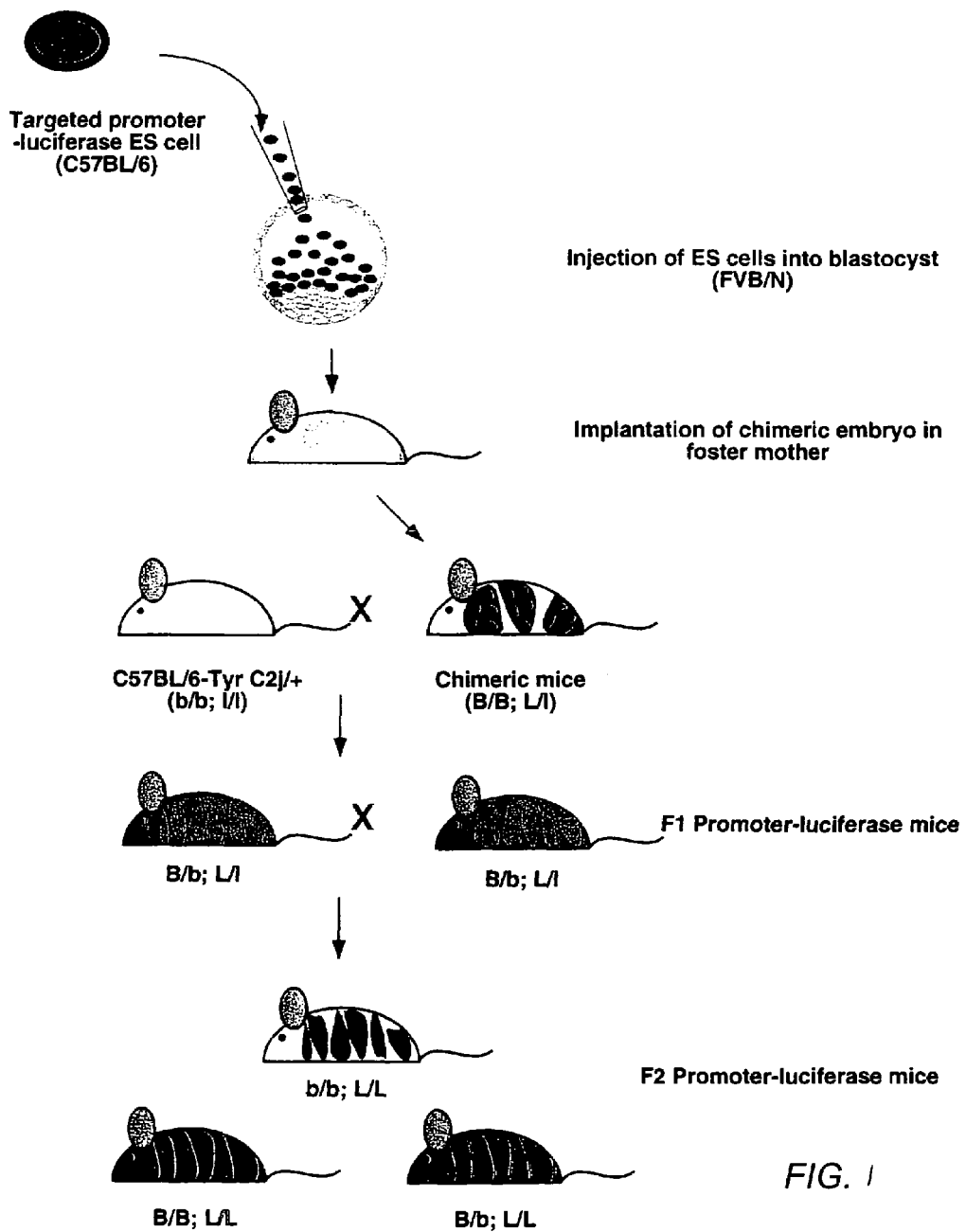
FIG. 1 depicts generation of targeted transgenic mice, using the targeting vectors described herein, and crosses using such transgenics as well as their offspring (F1, first generation; F2, second generation).

The practice of the present invention will employ, unless otherwise indicated, conventional methods of chemistry, biochemistry, molecular biology, immunology and pharmacology, within the skill of the art. Such techniques are explained fully in the literature. See, e.g., *Remington's Pharmaceutical Sciences,* 18th Edition (Easton, Pa.: Mack Publishing Company, 1990); *Handbook of Experimental Immunology*, Vols. I-IV (D. M. Weir and C.C. Blackwell, eds., 1986, Blackwell Scientific Publications); Ausubel, F. M., et al., *Current Protocols in Molecular Biology*, John Wiley and Sons, Inc., Media Pa.; and Sambrook, et al., *Molecular Cloning: A Laboratory Manual* (2nd Edition, 1989); the series METHODS IN ENZYMOLOGY (Academic Press, Inc.); PCR 2: A PRACTICAL APPROACH (M. J. McPherson, B. D. Hames and G. R. Taylor eds., 1995) and ANIMAL CELL CULTURE (R. I. Freshney. Ed., 1987).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise. Thus, for example, reference to a compound can include a mixture of two or more such agents.

1.0.0 Definitions

In describing the present invention, the following terms will be employed, and are intended to be defined as indicated below. Unless otherwise indicated, all terms used herein have the same meaning as they would to one skilled in the art of the present invention.

The terms "nucleic acid molecule" and "polynucleotide" are used interchangeably to and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term polynucleotide sequence is the alphabetical representation of a polynucleotide molecule. This alphabetical representation can be input into databases in a computer having a central processing unit and used for bioinformatics applications such as functional genomics and homology searching.

A "coding sequence" or a sequence which "encodes" a selected polypeptide, is a nucleic acid molecule which is transcribed (in the case of DNA) and translated (in the case of mRNA) into a polypeptide, for example, in vivo when placed under the control of appropriate regulatory sequences (or control elements). The boundaries of the coding sequence are typically determined by a start codon at the 5' (amino) terminus and a translation stop codon at the 3' (carboxy) terminus. A coding sequence can include, but is not limited to, cDNA from viral, procaryotic or eucaryotic MRNA, genomic DNA sequences from viral or procaryotic DNA, and even synthetic DNA sequences. A transcription termination sequence may be located 3' to the coding sequence. Other control elements may also be associated with a coding sequence. A DNA sequence encoding a polypeptide can be optimized for expression in a selected cell by using the codons preferred by the selected cell to represent the DNA copy of the desired polypeptide coding sequence. Encoded by refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences which are immunologically identifiable with a polypeptide encoded by the sequence.

Typical control elements or expression control elements or regulatory sequences, include, but are not limited to, transcription promoters, transcription enhancer elements, transcription termination signals, polyadenylation sequences (located 3' to the translation stop codon), sequences for optimization of initiation of translation (located 5' to the coding sequence), translation enhancing sequences, and translation termination sequences. Transcription promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is induced by an analyte, cofactor, regulatory protein, etc.), and constitutive promoters.

Expression enhancing sequences typically refer to control elements that improve transcription or translation of a polynucleotide relative to the expression level in the absence of such control elements (for example, promoters, promoter enhancers, enhancer elements, and translational enhancers (e.g., Shine and Delagarno sequences)).

Purified polynucleotide refers to a polynucleotide of interest or fragment thereof which is essentially free, e.g., contains less than about 50%, preferably less than about 70%, and more preferably less than about 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

A "heterologous sequence" as used herein is typically refers to either (i) a nucleic acid sequence that is not normally found in the cell or organism of interest, or (ii) a nucleic acid sequence introduced at a genomic site wherein the nucleic acid sequence does not normally occur in nature at that site. For example, a DNA sequence encoding a polypetide can be obtained from yeast and introduced into a bacterial cell. In this case the yeast DNA sequence is "heterologous" to the native DNA of the bacterial cell. Alternatively, a promoter sequence from a Tie2 gene can be introduced into the genomic location of afosB gene. In this case the Tie2 promoter sequence is "heterologous" to the nativefosB genomic sequence.

A "polypeptide" is used in it broadest sense to refer to a compound of two or more subunit amino acids, amino acid analogs, or other peptidomimetics. The subunits may be linked by peptide bonds or by other bonds, for example ester, ether, etc. As used herein, the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is typically called a polypeptide or a protein.

"Operably linked" refers to an arrangement of elements wherein the components so described are configured so as to perform their usual function. Thus, a given promoter that is operably linked to a coding sequence (e.g., a reporter expression cassette) is capable of effecting the expression of the coding sequence when the proper enzymes are present. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

"Recombinant" as used herein to describe a nucleic acid molecule means a polynucleotide of genomic, cDNA, semi-synthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting procaryotic microorganisms or eucaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms. An "isolated polynucleotide" molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith.

Techniques for determining nucleic acid and amino acid sequence identity also are known in the art. Typically, such techniques include determining the nucleotide sequence of the mRNA for a gene and/or determining the amino acid sequence encoded thereby, and comparing these sequences to a second nucleotide or amino acid sequence. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An exemplary implementation of this algorithm to determine percent identity of a sequence is provided by the Genetics Computer Group (Madison, WI) in the Best Fit utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the AMatch@ value reflects sequence identity. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST.

Alternatively, the degree of sequence similarity between polynucleotides can be determined by hybridization of polynucleotides under conditions that form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80%-85%, preferably at least about 85%-90%, more preferably at least about 90%-95%, and most preferably at least about 95%-98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence selectively hybridize or bind, to each other to form a hybrid molecule. A nucleic acid molecule that is capable of hybridizing selectively to a target sequence under moderately stringent typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

A vector is capable of transferring gene sequences to target cells. Typically, "vector construct," expression vector and "gene transfer vector," mean any nucleic acid construct capable of directing the expression of a gene of interest and which can transfer gene sequences to target cells. Thus, the term includes cloning, and expression vehicles, as well as integrating vectors.

"Nucleic acid expression vector" or "expression cassette" refers to an assembly which is capable of directing the expression of a sequence or gene of interest. The nucleic acid expression vector includes a promoter (typically with associated expression control sequences) which is operably linked to the sequences or gene(s) of interest. Other control elements may be present as well. Expression cassettes described herein may be contained within a plasmid construct. In addition to the components of the expression cassette, the plasmid construct may also include a bacterial origin of replication, one or more selectable markers, a signal which allows the plasmid construct to exist as single-stranded DNA (e.g., a M13 origin of replication), a multiple cloning site, and a "mammalian" origin of replication (e.g., a SV40 or adenovirus origin of replication).

An "expression cassette" comprises any nucleic acid construct capable of directing the expression of a gene/coding sequence of interest. Such cassettes can be constructed into a "vector," "vector construct," "expression vector," or "gene transfer vector," in order to transfer the expression cassette into target cells. Thus, the term includes cloning and expression vehicles, as well as viral vectors.

Light-generating is defined as capable of generating light through a chemical reaction or through the absorption of radiation.

A light generating protein or light-emitting protein is a protein capable of generating light in the visible spectrum (between approximately 350 nm and 800 nm). Examples include bioluminescent protiens such as luciferases, e.g., bacterial and firefly luciferases, as well as fluorescent proteins such as green fluorescent protein (GFP).

Luciferase unless stated otherwise, includes prokaryotic and eukaryotic luciferases, as well as variants possessing varied or altered optical properties, such as luciferases that produce different colors of light (e.g., Kajiyama, N., and Nakano, E., *Protein Engineering* 4(6):691-693 (1991)). Lux refers to prokaryotic genes associated with luciferase and photon emission. luc refers to eukaryotic genes associated with luciferase and photon emission.

Light is defined herein, unless stated otherwise, as electromagnetic radiation having a wavelength of between about 300 nm and about 1100 nm.

Animal as used herein typically refers to a non-human mammal, including, without limitation, farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

A transgenic animal refers to a genetically engineered animal or offspring of genetically engineered animals. A transgenic animal usually contains material from at least one unrelated organism, such as from a virus, plant, or other animal. The non-human animals of the invention include vertebrates such as rodents, non-human primates, sheep, dogs, cows, amphibians, birds, fish, insects, reptiles, etc. The term chimeric animal@ is used to refer to animals in which the heterologous gene is found, or in which the heterologous gene is expressed in some but not all cells of the animal.

Analyte as used herein refers to any compound or substance whose effects (e.g., induction or repression of a specific promoter) can be evaluated using the test animals and methods of the present invention. Such analytes include, but are not limited to, drugs, chemical compounds, pharmaceutical compounds, polypeptides, peptides, polynucleotides, and polynucleotide analogs. Many organizations (e.g., the National Institutes of Health, pharmaceutical and chemical corporations) have large libraries of chemical or biological compounds from natural or synthetic processes, or fermentation broths or extracts. Such compounds/analytes can be employed in the practice of the present invention.

As used herein, the term positive selection marker refers to a gene encoding a product that enables only the cells that carry the gene to survive and/or grow under certain conditions. For example, plant and animal cells that express the introduced neomycin resistance ($Neo^r$) gene are resistant to the compound G418. Cells that do not carry the $Neo^r$ gene marker are killed by G418. Other positive selection markers will be known to those of skill in the art. Typically, positive selection markers encode products that can be readily assayed. Thus, positive selection markers can be used to determine whether a particular DNA construct has been introduced into a cell, organ or tissue.

Negative selection marker refers to gene encoding a product which can be used to selectively kill and/or inhibit growth of cells under certain conditions. Non-limiting examples of negative selection inserts include a herpes simplex virus (HSV)-thymidine kinase (TK) gene. Cells containing an active HSV-TK gene are incapable of growing in the presence of gangcylovir or similar agents. Thus, depending on the substrate, some gene products can act as either positive or negative selection markers. The term homologous recombination refers to the exchange of DNA fragments between two DNA molecules or chromatids at the site of essentially identical nucleotide sequences. It is understood that substantially homologous sequences can accommodate insertions, deletions, and substitutions in the nucleotide sequence. Thus, linear sequences of nucleotides can be essentially identical even if some of the nucleotide residues do not precisely correspond or align (see, above).

A knock-out mutation refers to partial or complete loss of expression of at least a portion the target gene. Examples of knock-out mutations include, but are not limited to, gene-replacement by heterologous sequences, gene disruption by heterologous sequences, and deletion of essential elements of the gene (e.g., promoter region, portions of a coding sequence). A knock-out mutation is typically identified by the phenotype generated by the mutation.

A single-copy gene as used herein refers to a gene represented in an organism's genome only by a single copy at a particular chromosomal locus. Accordingly, a diploid organism has two copies of the gene and both copies occur at the same chromosomal location.

A gene as used in the context of the present invention is a sequence of nucleotides in a genetic nucleic acid (chromosome, plasmid, etc.) with which a genetic function is associated. A gene is a hereditary unit, for example of an organism, comprising a polynucleotide sequence (e.g., a DNA sequence for mammals) that occupies a specific physical location (a gene locus or genetic locus) within the genome of an organism. A gene can encode an expressed product, such as a polypeptide or a polynucleotide (e.g., tRNA). Alternatively, a gene may define a genomic location for a particular event/function, such as the binding of proteins and/or nucleic acids (e.g., phage attachment sites), wherein the gene does not encode an expressed product. Typically, a gene includes coding sequences, such as, polypeptide encoding sequences, and non-coding sequences, such as, promoter sequences, polyadenlyation sequences, transcriptional regulatory sequences (e.g., enhancer sequences). Many eucaryotic genes have exons (coding sequences) interrupted by introns (non-coding sequences). In certain cases, a gene may share sequences with another gene(s) (e.g., overlapping genes).

Isogenic means two or more organisms or cells that are considered to be genetically identical. Substantially isogenic means two or more organisms or cells wherein, at the majority of genetic loci (e.g., greater than 99.000%, preferably more than 99.900%, more preferably greater than 99.990%, even more preferably greater than 99.999%), there exists genetic identity between the organisms or cells being compared. In the context of the present invention, two organisms (for example, mice) are considered to be substantially isogenic if, for example, inserted transgenes are the primary differences between the genetic make-up of the mice being compared. Further, if, for example, the genetic backgrounds of the mice being compared are the same with the exception that one of the mice has one or several defined mutation(s) (for example, affecting coat color), then these mice are considered to be substantially isogenic. An example of two strains of substantially isogenic mice are C57BL/6 and C57BL/6-Tyr C2j/+.

A pseudogene as used herein, refers to a type of gene sequence found in the genomes, typically, of eucaryotes, where the sequence closely resembles a known functional gene, but differs in that the pseudogene is non-functional. For example, the pseudogene sequence may contain several stop codons in what would correspond to an open reading frame in the functional gene. Pseudogenes can also have deletions or insertions relative to their corresponding functional gene. If, for example, in a genome there is a functional gene and a related pseudogene, the functional gene is considered to be a single-copy gene (accordingly, the pseudogene is considered to be single-copy as well).

A non-essential gene refers to a gene whose deletion, disruption, elimination, reduction of gene function, or mutation is non-lethal, and does not obviously adversely affect the organism's ability to mature and reproduce. A non-essential gene with no phenotype refers to a non-essential gene whose deletion, disruption, elimination, reduction of gene function or mutation has no deleterious effect on the organism. Typically there are no phenotypically reflected gene dosage effects associated with modification of a non-essential gene with no phenotype—for example, deletion, disruption or mutation of both copies of a non-essential gene with no phenotype in a diploid organism has essentially the same effect as deletion, disruption, or mutation of one of the two copies present in the diploid organism. In the context of the present invention, a non-essential gene is typically one whose function has been eliminated (e.g., by a deletion mutation) and such elimination of function was non-lethal and the organism developed, matured, and was able to reproduce.

The native sequence or wild-type sequence of a gene is the polynucleotide sequence that comprises the genetic locus corresponding to the gene, e.g., all regulatory and open-reading frame coding sequences required for expression of a completely functional gene product as they are present in the wild-type genome of an organism. The native sequence of a gene can include, for example, transcriptional promoter sequences, translation enhancing sequences, introns, exons, and poly-A processing signal sites. It is noted that in the general population, wild-type genes may include multiple prevalent versions that contain alterations in sequence relative to each other and yet do not cause a discernible pathological effect. These variations are designated polymorphisms or allelic variations.

By "replacement sequence" is meant a polynucleotide sequence that is substituted for at least a portion of the native or wild-type sequence of a gene.

Linear vector or linearized vector, as used herein, is a vector having two ends. For example, circular vectors, such as plasmids, can be linearized by digestion with a restriction endonuclease that cuts at a single site in the plasmid. Preferably, the targeting vectors described herein are linearized such that the ends are not within the targeting sequences.

A cohort is used herein as a group of individuals having a statistical factor in common. In one aspect of the present invention, the statistical factor in common is that the individuals are substantially isogenic.

Opaque medium is used herein to refer to a medium that is "traditionally" opaque, not necessarily absolutely opaque. Accordingly, an opaque medium is defined as a medium that is commonly considered to be neither transparent nor translucent, and includes items such as a wood board, and flesh and skin of a mammal.

2.0.0 Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

2.1.0 General Overview of the Invention

The present invention provides a powerful new tool for analyzing biochemical pathways and physiological functions (e.g., toxicity, inflammation, pain, development, oncogenesis, apoptosis, etc.) both in vivo and in vitro. Using this unique approach, termed in vivo differential display (IVDD), gene expression in living animals can be readily studied. IVDD has many uses, including, but certainly not limited to, drug testing and development and toxicological testing for chemicals.

During virtually all non-normal physiological states, organisms activate (induce) specific genes or groups of genes. Thus, infectious agents, pathological conditions, environmental and/or toxic stimuli may induce the expression of certain genes associated with a particular biochemical pathway or physiological condition.

Genes, and promoters derived from these genes, that are induced by the aforementioned stimuli can be identified as described herein. For example, subtractive hybridization can be used to determine which transcripts are activated (or are overexpressed) when the cells or animals are exposed to the stimuli of interest.

Among a group of genes know to be induced in response to exposure to certain toxic and/or environmental stimuli are heat-shock genes or genes induced by UV damage by induction of DNA repair genes. Genes which respond in a characteristic manner to such environmental/toxic stimuli have been called damage-inducible or stress-related genes (MacGregor, J. T., et al, *Fundamental and Applied Toxicology*, 26:156-173, 1995). Typically the expression products of these genes are involved in buffering the organism from the stress associated with the induction of the gene(s) or have a role in detoxification of the organism from damage resulting from exposure to the stimuli. Toxins can be the result of cellular damage (such as the formation of thymine dimers in response to UV light) or toxins may be the direct cause of adverse effects on a cell type, group of cells, or organ systems within a subject. Some of the ways products of these stress-induced genes are involved in detoxification include, but are not limited to, direct neutralization of a toxic substance (or related metabolic products) by chemical modification; elimination of such a substance (or related metabolic products) from affected cells (for example, transport out of the cell); or repairing damage caused by the substance (or related metabolic products).

There are numerous examples of toxin mediated cellular damage that induce expression of stress-related genes, including, but not limited to, the following: damage to cellular DNA, osmotic shock, oxidation of lipids, disruption (e.g., uncoupling) of electron transport, membrane damage (e.g., permeabilization). Many stress-related genes have been identified in a broad spectrum of procaryotic and eucaryotic organisms. Further, the sequences of many of these genes (including coding sequences for the gene product and shared control elements) are known in the art. A high degree of conservation across phyla has been seen for cellular responses to stress. For example, the genes encoding heat shock proteins represent one such highly conserved class of genes (Hunt, C., and Morimoto, R., *Proc. Natl. Acad. Sci.* (USA) 82:6455-6459, 1985).

There are also numerous genes which have been shown to be involved in the following physiological functions: pain and/or inflammation (e.g., endorphins and enkephalins); organ inflammation (TGF-beta1); fever (IL-1 alpha/beta; TNF alpha/beta, IFN alpha, IL-6); cell proliferation (PCNA, TNF); development (bmp4—defective gastrulation, mesoderm formation, bmp5—skeletal defects, bmp7—kidney, eye, skeletal); drug metabolism (e.g., oxidation, NO (nitric oxide) synthesis and degradation; N-acetylation; and S-methylation); apoptosis (e.g., FAS, ICE, Bax); infectious diseases (e.g., chalmydia, toxoplasma); carcinogenesis (e.g., tumor suppressor genes, oncogenes, and proto-oncogenes); cell necrosis (TNF, TGF-beta1); oncogenesis and angiogenesis (e.g., heparanase, ApoB100, CETP, sPLA2, TIE2, VEGF genes, and VEGFR genes).

The control elements of the genes of interest are operably linked to reporter genes to create chimeric genes that used to generate transgenic animals (for example, mice). These transgenic animals can then serve as test animals for example, for toxicology or stress testing. Induction of expression of these genes can be evaluated using non-invasive imaging.

Non-invasive imaging and/or detecting of light-emitting conjugates in mammalian subjects was described in co-owned U.S. Pat. No. 5,650,135, by Contag, et al., issued Jul. 22, 1997, and herein incorporated by reference. This imaging technology can be used in the practice of the present invention in view of the teachings of the present specification.

Various forms of the different embodiments of the invention, described herein, may be combined.

2.1.1 Toxicology

Thus, in one aspect, the present invention relates to animal test systems and methods for toxicology studies of an analyte of interest. In the practice of the present invention, transgenic mammals are constructed where control elements, for example, a promoter or transcriptional regulatory sequence, of two or more stress-induced genes are operably linked to reporter gene coding sequences (for example, luciferase). An appropriate substrate for the reporter gene product is administered to the animal in addition to an analyte of interest. The order of administration of these two substances can be empirically determined for each analyte of interest. Induction of expression mediated by any of the control elements is then evaluated by noninvasive imaging methods using the whole animal.

In one aspect of the present invention, transgenic animals described herein can be used to evaluate the in vivo effects of high production volume (HPV) chemicals, for example, by examining the effects of HPVs on expression of toxicity related genes. To date there are approximately 3,000 HPV chemicals within the set of non-polymeric chemicals (polymeric chemicals tend to be poorly absorbed by organisms and thus generally have low toxicity). Before the present invention there has been no routine, effective way to evaluate toxicity of these chemicals in vivo, which takes into account toxicity of not only the chemical itself, but of metabolites thereof (e.g., breakdown products).

Chemical producers and importers have been invited by the United States Environmental Protection Agency (EPA) to provide basic toxicity information on their high production volume (HPV) chemicals. HPV chemicals are chemicals produced in or imported to the United States in amounts over 1 million pounds per year. Each chemical companies participating in the voluntary program will make a commitment to identify chemicals that the company will adopt for testing. Following the guidelines established by EPA, participating companies will perform the following tasks: assessment of the adequacy of existing data; design and submission of test plans; provide test results as generated; and prepare summaries of the data characterizing each chemical. Currently, the voluntary program uses the same tests, testing protocols, and basic information summary formats employed by the Screening Information Data Set (SIDS) program. SIDS is a cooperative, international effort to secure basic toxicity information on HPV chemicals worldwide. Accordingly, information prepared for the U.S. domestic program will be acceptable in the international effort.

Of the approximately 3,000 chemicals that the U.S. imports or produces at more than 1 million lbs./yr., a recent EPA analysis finds that 43% of these high production volume chemicals have no testing data on basic toxicity and only seven percent have a full set of basic test data (http://www.epa.gov/opptintr/chemrtk). This lack of test data compromises the public's right to know about the chemicals that are found in the environment, homes, workplaces, and products.

There are six basic tests which have been internationally agreed to for screening high production volume (HPV) chemicals for toxicity. The tests agreed to under the Organization for Economic Cooperation and Development's Screening Information Data Set (OECD/SIDS) program include the following: acute toxicity; chronic toxicity; developmental/reproductive toxicity; mutagenicity; ecotoxicity and environmental fate. Several of these tests rely on animal models where the animal must be sacrificed to obtain toxicity data. The transgenic animals described herein are useful for toxicity testing and avoid the need for a death as the end-point model. Accordingly, use of the transgenic animals of the present invention to evaluate toxicity will provide for a more humane means of toxicity testing. Further, because death as the endpoint is not always necessary using transgenic animals carrying the reporter expression cassettes of the present invention, costs associated with toxicity testing in live animals can likely be reduced.

The EPA's Chemical Hazard Data Availability Study found major gaps in the basic information that is readily available to the public. Most consumers assume that basic toxicity testing is available and that all chemicals in commerce today are safe. A recent EPA study has found that this is not a prudent assumption. The EPA has reviewed the publicly available data on these chemicals and has learned that most of them may have never been tested to determine how toxic they are to humans or the environment. The EPA cannot begin to judge the hazards and risks of HPV consumer chemicals without basic information, and, in fact, substantially more detailed and exhaustive testing is needed to assess these high exposure chemicals (http://www.epa.gov/opptintr/chemrtk). It is clear that companies need to do more to address this problem.

SIDS tests do not fully measure a chemical's toxicity. The tests only provide a minimum set of information that can be used to determine the relative hazards of chemicals and to judge if additional testing is necessary. However, the transgenic animals of the present invention provide models for in vivo toxicity testing that can greatly expand the information available about the hazards of these chemicals and their metabolites.

OSHA sets Permissible Exposure Limits (PELs) for hazardous chemicals in the workplace. It seems reasonable to expect that chemicals with PELs have been thoroughly tested at least for human health effects. However, even the high volume chemicals with PELs have significant data gaps from the human health portion of the basic screening test set. Only 53% of these high volume chemicals with PELs have basic screening tests for all four of the human health endpoints. In contrast, only 5% of the non-PEL HPV chemicals had all four health effects tests and 49% had no health test data available (http://www.epa.gov/opptintr/chemrtk). Thus, the bulk of HPV chemicals without PELs lack even the minimal data needed to support development of a PEL value to protect workers. The transgenic animals of the present invention provide means for testing toxicity that provide specific, in vivo data concerning toxicity not only of the chemicals themselves, but of metabolites of these chemicals as well.

Finally, chemicals contained in consumer products are a major concern due to the likelihood of their exposure to children, as well as other sensitive populations (e.g., pregnant women and health-compromised individuals). Although the chemical industry has completed basic testing for more of these chemicals than is the case for other HPV chemicals, a more complete evaluation of in vivo toxicity using the transgenic animals of the present invention would be desirable. Given the great exposure potential of consumer products, significantly greater amounts of testing are needed to assess the risks of such chemicals. The transgenic animals described herein help to meet this need.

In a related aspect of the present invention, the transgenic animals described herein can be used to evaluate the in vivo effects of endocrine disruptors (ED). EDs are typically chemicals that interfere with the normal functioning of the endocrine system (including, for example, many pesticides and fertilizers). The increasing need for evaluation of HPV and potential endocrine disruptors, both in view of public interest and mandates for testing from the U.S. Federal Government, are likely to be met by the transgenic animals and accompanying compound screening methods of the present invention.

Several classes of stress-related genes and the promoters thereof are described in more detail below. Control elements (e.g., promoters and/or expression regulatory elements) derived from genes of interest are operably linked to a coding sequence of a light generating protein, for example, luciferase. Exemplary genes and regulatory elements include, but are not limited to, the following: Nitric oxide synthetase (NOS)—Immunologic NOS (iNOS), Neuronal NOS (nNOS),Endothelial NOS (eNOS); Cytochrome P450 (10)— 2D5, 2C19, 3A2, 3A4, 2C9, 2B1, 2B4, 2E1, 1A1, 4A2; N-acetyl transferase (NAT)—NAT1, NAT2; S-methyl transferase—TMT, TPMT; Flavin-containing monooxygenase (FMO)—FMO1, FMO2, FMO3, FMO4, FMO5; Cyclooxygenase (COX)—COX-1 (constitutive), COX-2 (inducible); Heat shock protein (HSP)—HSP 23, HSP 70; Apoptosis-related—bak, p21, bax; Monamine oxidase (MO)—MAO A, MAO B; Glutathione S-transferase (GST)—GSTa, GSTm, GSTp, GSTs, GSTq; UDP-glucuronyltransferase (UGT)— UGT1, UGT2; S-methyl transferase (MT)—Thiol-MT (MT), Thioether-S-MT (TEMT), Thiopurine-MT (TPMT); Alcohol dehydrogenase (ADH)—ADH1, ADH2, ADH3, ADH4, ADH5, ADH6, ADH7; Aldehyde dehydrogenase (ALDH)— Class 1 ALDH, Class 2 ALDH, Class 3 ALDH; Bone morphogenic protein (BMP)—BMP-4; and, Endocrine disruptor—Estrogen response element (ERE), Progesterone RE (PRE), Androgen RE (ARE), Thyroid Hormone RE (THRE), Gonadotropin RE (GnRE).

Several classes of stress-related genes, and the promoters/control elements thereof, are described in more detail below.

2.1.2 Biochemical Pathways

In another aspect, the invention relates to test systems for studying the effect of an analyte on a biochemical pathway (e.g., multi-step and branched pathways). Control elements (e.g., promoters and/or expression regulatory elements) derived from various genes in the selected pathway are operably linked to a luciferase encoding sequence. In one embodiment, each gene is linked to a luciferase of a different wavelength, and each construct is then introduced into a whole animal or into cells. An appropriate substrate for the reporter gene product is administered to the animal or cells in addition to an analyte of interest. The order of administration of these two substances can be empirically determined for each analyte of interest. Induction of expression mediated by any of the control elements is then evaluated in cells or by non-invasive imaging methods using the whole animal.

2.1.3 Animal Models for Disease States

The present invention also provides test systems for studying a wide variety of physiological functions. Thus, in addition to the toxicology studies, the test systems described herein are useful for studying (e.g., creating animal models of) pain, inflammation, apoptosis, angiogenesis, developmental defects, oncogenesis and specific disease states. Numerous genes associated with all of these pathways and functions have been identified. Using the methods and compositions described herein, the control elements from the known gene of interest is operably linked to a luciferase encoding sequence to make an expression cassette which allows for monitoring of expression of the gene interest. Moreover, luciferase allows in vivo monitoring of gene expression, for example in response to administration of an analyte of interest, in transgenic mammals created using the expression cassette.

2.1.4 Further Animal Model Test Systems

The present invention is also useful in developing test systems where the identity of the gene of interest is not known. In such instances, the gene of interest can be identified in a variety of ways. For example, to identify genes associated with specific diseases, such as infection, RNA is isolated from cells affected by the disease (e.g., host cells infected with an infectious agent such as chalmydia). This RNA is then made into cDNA and screened, for example using chip arrays, against a normal, undiseased control. This allows for identification of transcripts that are upregulated or overexpressed in the affected cells. Control elements that are associated with the overexpressed transcripts are then identified and the control elements operably linked to luciferase encoding sequences. As described above, a suitable substrate and analyte of interest are administered and expression of the luciferases monitored.

2.1.5 Target Validation Using Animal Model Test Systems

Two primary reasons why most drugs fail when moving from in vitro studies to application in animals are as follows: (a) the target chosen for screening (for example, a selected cell type maintained in culture or effects of expression of a selected gene) was not as predictive of in vivo effects as was originally believed; and (b) toxicity of the drug being tested was unacceptable in a whole animal system and the toxicity effects were not seen or were under-estimated in the in vitro study system.

One advantage of the present invention is the ability to correlate a reporter gene(s) to function, i.e., detection of the reporter correlates to the desired target effect (such as toxicity) in the animal.

The biochemistry of the metabolism of foreign compounds and the individual roles played cytochrome P450 (CYP) enzymes in this metabolism are important areas of molecular pharmacology and toxicology. Target validation of specific pathways used by a living animal in the metabolism of such compounds is one advantage of the transgenic animals of the present invention. The transgenic animals described herein provide an important advance in the ability to evaluate the effects of foreign compounds in vivo. In one aspect, the transgenic animals described herein allow the evaluation of the mechanisms through which, for example, xenochemicals induce the expression of hepatic P450 enzymes. Exemplary genes from which promoter and further control elements can be derived include, but are not limited to, the following: nuclear receptor superfamily members (e.g., PXR, preegnenolone X receptor; PPAR, peroxisome proliferator activated receptor, including, alpha, beta, and gamma isotypes; and RXR, retinoid X-receptor); genes involved in hepatic gluconeogenesis (e.g., PEPCK, phosphoenolpyruvate carboxykinase gene); other nuclear receptors (such as, LXR and FXR, which are, respectively, activated by oxysterols and bile acids); and hepatic P450s (e.g., CYP2, CYP3, and CYP4). Further, all five currently known P450-regulatory nuclear receptors belong to the same nuclear receptor gene family (NR1). These receptors share a common heterodimerization partner, retinoid X-receptor (RXR) and are subject to cross-interactions with other nuclear receptors and with other intracellular signaling pathways, including those activated by certain cytokines and growth factors.

Promoters and other regulatory elements derived from these genes (for example, upstream regulatory regions of the various hepatic p450s, or RXR-containing regions) are each individually operably linked to a reporter, e.g., a light generating protein, to create expression cassettes. A group of such p450-related expression cassettes may be designated as a Toxicity Evaluation Expression Cassette Panel. These expression cassettes are then used to generate, for example, a transgenic animal or cohort of animals. In one embodiment, one animal may contain multiple expression cassettes (e.g., expression cassettes containing promoters/regulatory elements from hepatic p450s CYP2, CYP3, and CYP4). Alternately, a cohort of animals may be generated where each animal contains one such expression cassettes or various combinations of expression cassettes. Such animals are then used to screen compounds of interest (e.g., xenochemicals) and to ascertain which genes are being activated (or repressed) in response to administration of the compound in a living transgenic animal. This approach allows identification of specific pathway activation(s) in response to, for example, a selected xenochemical providing a means of target validation of specific pathways used by a living animal in the metabolism of such compounds (for example, preferential induction of CYP2 relative to CYP3 and CYP4.) Two important advantages of the transgenic animals of the present invention is that death is not the evaluation-point (as it is in the determination of an LD50) and animals can be reused for testing of either other concentrations of the same compound or testing of other compounds after clearance of the first compound. Accordingly, these transgenic animals provide more humane testing methods, as well as, cost savings.

Another example of target validation, may involve labeling pathways involved in the progression or termination of an infectious disease. For example, a transgenic animal of the present invention may contain three expression cassettes as follows: expression regulatory sequences derived from an alpha interferon gene operably linked to coding sequences for a first light generating protein; expression regulatory sequences derived from a beta interferon gene operably linked to a coding sequences for second light generating protein; and expression regulatory sequences derived from a gamma interferon gene operably linked to coding sequences for a third light generating protein; wherein the three light generating proteins emit light at three different wavelengths. An infectious agent (e.g., chlamydia) is administered to the mouse and the relative levels of activation (or repression) of the different interferon regulatory sequences is evaluated (see below).

In response to the administration of the infectious agent it is observed, for example, that production of gamma interferon is induced (i.e., production of the light generating protein associated with the gamma interferon regulatory elements is observed). This suggests that one target of the infectious agent is induction of gamma interferon. To further validate target pathways being affected by the infectious agent additional mice may be used. In this example, such additional mice may include individual transgenic mice or cohorts of transgenic mice having expression cassettes containing regulatory sequences of a variety of genes subject to or related to gamma interferon regulation or production. Such expression cassettes may, for example, include promoters and/or regulatory sequences derived from the following genes: CD95 (Fas); CD95 ligand (Fas-L); class II major histocompatability complex; B7-1; inducible protein 10 (IP-10); and inducible nitric oxide synthase (iNOS). In this manner specific pathways being affected by the infectious agent can be identified.

Yet another example of pathway labeling that can be used for target validation in a living animal is a panel of expression cassettes assembled to represent a variety of different pathways commonly involved in pathogenesis of infectious agents (e.g., chlamydia or trypanosomes). Such a panel of expression cassettes may include, for example, promoters and/or inducible (or repressible) regulatory sequences involved in the expression of the following genes: immediate-early gene c-fos (an indicator of cellular activity); tumor necrosis factor alpha (TNF-alpha); interleukin 6 (IL-6, an exemplary pro-inflammatory cytokine); inhibitory factor kappa B alpha (IkappaBalpha B an indicator of the nuclear factor kappaB activity, the transcription factor of numerous proinflammatory molecules); interleukin 12 (IL-12); macrophage inflammatory protein-2 (MIP-2); and inducible nitric oxide synthase (iNOS). As described herein, such regulatory sequences may be operably linked to light generating proteins that emit light at different wavelengths (typically when multiple expression cassettes are used to generate a single transgenic animal) or similar wavelengths (typically when the expression cassettes are used to generate cohorts of animals). Light production associated with one or more of such regulatory elements can indicate a target pathway.

2.2.0 Advantages

Advantages of the present invention include, but are not limited to, (i) obtaining in vivo information about biochemical pathways and physiological functions, for both characterized and uncharacterized genes; (ii) obtaining in vivo information about the molecular damage underlying toxic effects thus improving the reliability of laboratory toxicology studies, (iii) obtaining test systems to study gene expression and drug development for specific diseases such as chlamydia; (iv) the presence of toxins and/or toxin-related cellular damage (caused by exposure to a toxin or toxic-stress) can be efficiently characterized and monitored; (v) help in determining the levels of an analyte that are effective and that can be tolerated by an animal, (vi) predicting drug efficacy and toxicity in humans, and (vii) providing means to examine not only the effects of a particular analyte, but also, effects of breakdown or modification products formed in vivo after administration of the analyte.

3.0.0 Expression Cassettes

In one aspect of the present invention, reporter gene expression cassettes are constructed using control elements (e.g., promoters) selected from a gene or groups of genes whose expression is known to be associated with a particular biochemical pathway or physiological function. In one aspect of the present invention, a group (or array) of expression cassettes is created. For example, an array of expression cassettes can be created for evaluating the toxicity of a selected compound, or, for creating a disease model mouse/mice.

The expression cassettes of the present invention can be assembled into panels, for example, a panel of at least two, preferably three, more preferably four or more (typically up to ten and usually not more than 15-50). Such panels are typically grouped by the type of genes from which the control elements, used in the creation of the expression cassettes, were derived. Groups of genes are described herein and include, but are not limited to, the following: stressinducible genes; apoptosis-related genes; angiogenesis-related genes; inflammation-related genes; genes whose expression is induced in a host in response to an infectious agent; oncogenesis-related genes; and development-related genes. Such panels of expression cassettes can be introduced into single or multiple animals. Further, animals may contain expression cassettes related to one or more panel. In this embodiment the different panels may each contain, for example, in its expression cassettes coding sequences for a light generating polypeptide that emits light at different wavelengths (accordingly expression of the reporter cassettes in the animal can be identified with their corresponding panel). Use of light generating polypeptides that emit light at different wavelengths is not necessary, however, and a single light generating polypeptide might be used, for example, in transgenic animals used for initial screenings.

The panels of expression cassettes of the present invention may also be formulated into a kit. Such kits may further include containers, instructions, and the expression cassettes that comprise the panel placed in one or more vector(s) useful in transformation or transfection methods (for example, vector(s) useful for transfection of ES cells).

3.1.0 Construction of Reporter Expression Cassettes

In one aspect of the present invention, reporter gene expression cassettes are constructed using control elements selected from a gene or groups of genes whose expression is known to be associated with a particular biochemical pathway or physiological function. For example, the control elements may be stress-inducible control elements selected from a gene or group of genes associated with cellular stress or toxicity. Thus, toxicity can be monitored in vivo by analyzing expression of the reporter gene. In addition, the control elements may be selected from a gene or group of genes associated with a biochemical pathway or a physiological function (e.g., pain/inflammation, infection, carcinogenesis, angiogenesis, development and the like).

Each gene is controlled by a unique promoter. However, genes that respond to a particular stimuli (e.g., stress, infection) can contain within their promoters a common response element (CRE) or, associated with their promoters, regulatory or control sequences involved with regulation of expression of the gene (e.g., induction or repression). In one aspect, upon the exposure of cells to a particular stimuli, the actions of transcription factors upon CREs are responsible for inducing expression of the collection of genes having the CRE of interest. CREs (or other regulatory or control elements associated with a selected gene) can be isolated (for example, by producing the sequence synthetically or by polymerase chain reaction amplification from a template; Mullis, K. B., U.S. Pat. No. 4,683,202, issued Jul. 28, 1987; Mullis, K. B., et al., U.S. Pat. No. 4,683,195, issued Jul. 28, 1987; both herein incorporated by reference) and operably linked to a minimal promoter and a reporter gene. In this case, the regulatory (or control) sequences confer the responsiveness to the construct, i.e., the promoter taken as a whole functions like a promoter derived from a selected gene.

The control element (e.g., a promoter) may be from the same species as the transgenic animal (e.g., mouse promoter used in construct to make transgenic mouse), from a different species (e.g., human promoter used in construct to make transgenic mouse), or a mixed control element (e.g., some control elements from a mouse promoter combined with some control elements of a human promoter). The control element can be derived from any gene of interest by methods known in the art (e.g., PCR using primers flanking the control sequences of interest). In one embodiment of the present invention, the promoter is derived from a gene whose expression is induced during angiogenesis, for example pathogenic angiogenesis like tumor development. Thus, when a tumor begins to develop in a transgenic animal carrying a vector construct of the present invention, the promoter is induced and the animal expresses, for example, luciferase, which can then be monitored in vivo.

Exemplary promoters for use in the present invention are selected such that they are functional in a cell type and/or animal into which they are being introduced.

Regulatory (or control) sequences can be obtained from a gene of interest by methods known in the art. For example, commercial databases (e.g., ENTREZ and GENBANK—National Center for Biotechnology Information, http://www.ncbi.nlm.nih.gov/; EMBL—The European Bioinformatics Institute, Hinxton, UK, http://www.ebi.ac.uk/) and contemporary scientific literature (MEDLINE B The National Library of Medicine, 8600 Rockville Pike, Bethesda, Md., http://www.nlm.nih.gov/) can be searched for information about a selected gene (e.g., iNOS) including locations of coding and regulatory sequences. Alternatively, methods of identifying regulatory sequences associated with a particular gene are known in the art, for example, deletion analysis or PCR amplification of fragments derived from 5' non-coding regions of a selected gene where these fragments are then operably linked to a reporter gene to identify regulatory (or control) sequences. Such reporter genes with associated regulatory sequences can be screened, for example, in cultured cells.

Reporter expression cassettes useful in the practice of the present invention can be constructed using any control element of interest operably linked to suitable reporter gene coding sequences. The expression cassettes can be used either directly or placed in any number of vectors in order to stably or transiently transfect cells with the expression cassette. In addition, the expression cassette can be used either directly for the generation of transgenic animals or placed in any number of vectors useful for the generation of transgenic animals. These animals (test animals) can then be used for examining the in vivo effects of a selected analyte (for example, a drug of interest) on expression mediated by the selected control element(s).

Construction of such expression cassettes, following the teachings of the present specification, utilizes methodologies well known in the art of molecular biology (see, for example, Ausubel or Maniatis). Before use of the expression cassette to generate a transgenic animal, the responsiveness of the expression cassette to the stress-inducer associated with selected control elements can be tested by introducing the expression cassette into a suitable cell line (e.g., primary cells, transformed cells, or immortalized cell lines).

The control elements of the genes of interest are operably linked to reporter genes to create chimeric genes (e.g., reporter expression cassettes) that are used to generate transgenic animals (for example, mice). These transgenic animals can then serve as test animals as described herein. Induction, repression, or any state of expression of such reporter expression cassettes genes can be evaluated using non-invasive imaging.

Various forms of the different embodiments of the invention, described herein, may be combined.

3.1.1 Control Elements Derived from Stress-Inducible Genes

Many stress-inducible genes have been identified, sequenced, and analyzed. Information about stress-related control elements is widely available. In the practice of the present invention stress-related control elements are selected, and operably linked to a reporter gene coding sequence, which results in the generation of chimeric genes where the reporter gene coding sequences (for example, sequences encoding a light generating polypeptide such as luciferase) are subject to the regulation provided by the stress-related control elements.

Prokaryotic and eukaryotic cells utilize sensory and signaling systems to obtain and transmit information from their environment to adjust cellular functions. External factors that trigger such molecular communications include nutrients, ions, drugs and other compounds, as well as, physical parameters (e.g., temperature). Stress imposed on cells can typically be considered any disturbance of a cells normal growth condition, and can include any deviation from optimal growth conditions.

The response to heat shock, for example, has been extensively studied (Mager, W.H., and De Kruijff, A. J., $Microbiol. Rev.$ 59(3):506-531, 1995; Hunt, C., and Morimoto, R., $Proc. Natl. Acad. Sci.$ (USA) 82:6455-6459, 1985). Accumulating evidence suggests that there is a role for the expression of heat shock proteins in a number of disease states , including inflammation and ischaema (Leppa, S., and Sistonen, L., $Ann. Med.$ 29(1):73-78, 1997). The heat shock response is aimed primarily at (i) protection and repair of cellular components, and (ii) partly at acquisition of heat tolerance.

Further, heat stress conditions induce a general response common to other metabolically adverse circumstances that lead to physiological perturbations (for example, osmotic or oxidative stress). The induction of gene expression in response to challenge by stress is primarily effected by the cell through transcription factors, their cognate promoter elements, and the modulation of the transcription factors activity for stress signal transduction. With respect to heat shock-induced expression, a great deal of information is available for both prokaryotic and eukaryotic organisms.

In addition, a large number of other stress-inducible genes have been characterized. These genes can be broadly categorized into five groups relating to the type of stress associated with induction of gene expression: inter- and intracellular potential; DNA related; protein related; energy related; and membrane related. Stress-inducible control elements have been widely characterized in the literature and sequences of some exemplary control elements have been summarized by Farr, et al. (U.S. Pat. No. 5,811,231, issued Sep. 22, 1998, herein incorporated by reference), Lindquist, S. (U.S. Pat. No. 5,827,685, issued Oct. 27, 1998, herein incorporated by reference), Kowalski, J., et al, (U.S. Pat. No. 5,733,745, issued Mar. 31, 1998, herein incorporated by reference), and MacGregor et al. (*Fundamental and Applied Toxicology* 26:156-173, 1995). Sequences of selected control elements associated with stress-induced or damage-related expression can also be obtained from sequence databases (e.g., GENBANK or ENTREZ, National Center for Biotechnology Information, National Institutes of Health, Bethesda, Md., US).

Following here are examples of stress-induced promoters useful in the practice of the present invention.

3.1.1.1 Control Elements of Stress-Related Genes Associated with DNA Function, Replication, and Repair DNA stress refers to alterations to deoxyribonucleic acid or to precursor nucleotides that result in a stress or toxicity to a cell. DNA stress includes, but is not limited to, DNA strand breaks, DNA strand cross-linking, DNA alkylation, exposure to DNA intercalating agents, both increased and decreased superhelicity, and oxidation or alkylation of nucleoside triphosphates. DNA stress can also be caused by inhibition of: DNA synthesis, DNA replication, mitosis, or meiosis. Further, exposure to the following conditions may also cause DNA stress: inflammatory agents, growth factors, tumor necrosis factor, tumor promoters, interferons, phorbol esters, hydrophobic cytotoxic drugs, mitogens, carcinogens, X-rays, and UV radiation.

DNA stress related promoters and response elements useful in the practice of the present invention include, but are not limited to, promoters of the DNA dependent PK, DNA repair genes, GADD45, FOS, XHF and GADD153 genes, and the TRE and p53RE response elements. The GADD45 gene encodes a growth arrest and DNA damage responsive protein. The gene is induced by UV irradiation, X-rays, and methyl methane sulfonate (MMS)(Zhan, Q., et al., *Mol. Cell Biol.*, 13:4242-4250, 1993). FOS encodes the oncogene protein c-fos. Components of its promoter are DNA stress-sensitive and induced by growth factors and tumor promoters (Haliday, E. M., *EMBO J.*, 10: 109-115, 1991; van Straaten, F., et al., *Proc. Natl. Acad. Sci. USA* 80:3183-3187, 1983). The XHF gene encodes collagenase. The XHF gene is activated by mitogenesis, inflammatory agents, UV radiation, and 12-O-tetradecanoyl-phorbol-13-acetate (TPA; a tumor promoter). (Angel, P., et al., *Mol. Cell. Biol.* 7:2256-2266, 1987.) Expression of the GADD153 gene is induced in response to DNA damaging agents and growth arresting signals agents (Luethy, J. D., and Holbrook, N. J., *Cancer Res.*, 52:5-10, 1992; Fornace, A. J., et al., *Mol. Cell. Biol.*, 9:4196-4203, 1989).

In addition to these genes several DNA stress related response elements are also useful in the practice of the present invention including TRE and p53RE. TRE is the TPA response element which responds to DNA stress induced by phorbol esters (Angel, P., et al., *Cell* 55:875-885, 1988). p53RE is the p53 response element which is induced by X-rays and MMS (Zahn, Q., et al., *Mol. Cell. Biol.* 13:4242-4250, 1993).

3.1.1.2 Control Elements of Stress-Related Genes Associated with Protein Damage and Alteration Damage to or alteration of cellular proteins (protein-related stress) includes, but is not limited to, alterations of polypeptides, alterations of individual amino acids, oxidation of individual amino acids, inhibition of enzymatic functions, perturbations of intracellular transport of proteins, denaturation of proteins, cross-linking of proteins, protein misfolding, chelation of protein cofactors, oxidation of inter- and intra-polypeptide chain bonds (such as disulfide bonds), alkylation of proteins, and protein damage (for example, caused by exposure to heavy metals or heat).

Control elements that respond to protein damage or alterations (protein-related stress) are also useful in the practice of the present invention. Such control elements include, but are not limited to, those which can be obtained from the following genes: JNK, p38, HO, GRP78, HSP70, MTIIA, JUN, and FOS. The GRP78 gene encodes a protein that is a major endoplasmic reticulum component. Expression of the GRP78 gene is induced by glycosylation blocks and misfolded proteins (Wooden, S. K., et al., *Mol. Cell. Biol.* 11:5612-5623, 1991; Resendez, E., et al., *Mol. Cell. Biol.* 5:1212-1219, 1985). The HSP70 gene encodes heat shock protein 70. The gene is induced by inhibitors of energy metabolism, heat, amino acid analogues, heavy metals, anoxia and denatured proteins (Mosser., D. D., et al, *Mol. Cell. Biol.* 8:4736-4744, 1988; Hunt, C. and Morimoto, R. I., *Proc. Natl. Acad. Sci USA* 82:6455-6459, 1985). The gene MT IIA encodes metallothionein IIA. Expression of the gene is induced by heavy metals and glucocorticoids (Karin, M. et al., *Nature* 299:797-802, 1982). MT 1A (Richards, R.I., et al, *Cell* 37:263-272, 1984) and MT III (Palmitter, R. D., et al., *Proc. Natl. Acad. Sci. USA* 89:6333-6337, 1992) are also metallothionein encoding genes that are induced by cadmium (a heavy metal). JUN (described above) and FOS (described below) also contain protein stress-responsive elements which are induced by heat.

3.1.1.3 Control Elements of Stress-Related Genes Associated with Cellular Potential A disruption of the normal reduction/oxidation potential ("redox") of a cell leads to expression of genes mediated by of a group of mammalian promoters. Redox or cellular potential stress includes increased levels of superoxides radicals, increased levels of peroxides—both hydrogen peroxide and organic peroxides—, decreased levels of glutathione and any other conditions which alter the redox potential of the cell, such as exposure to strong reducing agents, some aromatic hydrocarbons, electrophilic compounds, aldehydes, intracellular thiols, steroids, methyl cholanthrene, phenobarbital and CCl sub 4. The term also includes any additional conditions which cause proliferation of peroxisomes.

Control elements associated with genes that respond to cellular potential stresses can be obtained from a variety of genes including, but not limited to, the following: HMO, CYP1A1, GST Ya, ALDHL, and JUN.

The HMO gene encodes heme oxygenase. Gene expression is induced by redox stresses including oxidative stress, hydrogen peroxides, and sodium arsenite (Keyse, S. T., and Tyrell, R. M., *Proc. Natl. Acad. Sci. USA,* 86:99-103, 1989). The CYP1A1 gene encodes cytochrome P450 1A1, an enzyme involved in polycyclic aromatic hydrocarbons metabolism. Gene expression is inducible by aromatic hydrocarbons, plant flavones and tetrachlorodibenzo-p-dioxin (TCDD) (Neuhold, L. A., et al., *Mol. Cell. Biol.*, 9:2378-2386, 1989; Fujii-Kuriyama, Y., et al., *The FASEB J.*, 6:706-710, 1992; Dixon, R. A., et al., *Biol. Rev.*, 61:239-241, 1986; Sogawa, K., et al., *Proc. Natl. Acad. Sci. USA* 83(21):8044-8048, 1986). The GST Ya gene encodes glutathione S-transferase Ya subunit. The stress-sensitive portion of the GST Ya promoter is strongly induced by electrophilic herbicides, insecticides and planar aromatic hydrocarbons. (Rushmore, T. H., et al., *Proc. Natl. Acad. Sci. USA,* 87:3826-3830, 1990). The ALDH 2 gene encodes aldehyde dehydrogenase. Gene expression is induced by aldehydes and peroxisome proliferators (Nebert, D. W., *Env. Health Persp.*, 88:13-25, 1990; Hsu, L. C., et al., *Proc. Natl. Acad. Sci. USA,* 82:3771-3775, 1985). JUN is an oncogene that encodes c-jun which participates in the formation of the AP-1 transcriptional activator complex. Stresses that activate expression of the JUN gene are superoxide radicals and UVA radiation. (De Groot, R., et al., *EMBO J.*, 10:2523-2532, 1991).

In addition to the above mentioned genes, there are known response elements associated with genes that respond to cellular potential stresses including, but not limited to, the following: ThRE, NFkBRE, XRE, RARE, PPRE, and ERE.

The thyroid hormone response element (ThRE) responds to stress induced by thyroid hormone and its analogs. (Beato, M., *Cell,* 56:335-344, 1989)., the disclosure of which is herein incorporated by reference. NFkBRE is a stress response element which encodes a transcription factor activated by intracellular thiols (Nelson, B., et al., *Molec. Cell. Biol.,* 8:3526-3531, 1988; Leung, K. and Nabel, G., *Nature,* 333:776-778, 1988; Schreck, R., et al., *EMBO J.,* 10:2247-2258, 1991). The XRE stress response element responds to xenobiotics, such as aromatic hydrocarbons (Rushmore, T. H., et al., *Proc. Natl. Acad. Sci. USA* 87:3826-3830, 1990). RARE is the retinoic acid response element which responds to the steroid hormone retinoic acid and analogs thereof (de The, H., et al., *Nature* 343:17-180, 199). PPRE is the peroxisome proliferation response element which is induced by peroxisome proliferators (Dreyer, C., et al., *Cell,* 68:879-887, 1992). ERE is the estrogen response element which responds to stress induced by estrogenic compounds. (Kumar, V., et al., *Cell,* 55:145-156, 1988).

3.1.1.4 Control Elements of Stress-Related Genes Associated with Membranes—Composition, Structure and Function Cell surface receptor-mediated stresses typically alter the transcription level of genes whose expression is regulated by the interaction of a cell surface receptor with a ligand. Control elements associated with genes that respond to cell surface receptor-mediated stress can be obtained from a variety of genes including, but not limited to, IL-1 alpha, IL-1 beta, TNF-alpha, G-CSF, GM-CSF, IL-3, IL-6, IL-8, IL-10, and ICAM-1. Interleukin (IL)-1 alpha gene encodes a cytokine. Expression of the gene is induced by lipopolysaccharide (LPS), PMA, mitogens, other cytokines, and UVB irradiation (Luger, T. A., et al., *J. Invest. Dermatol.* 95:1005-1045, 1990; Furutani, Y., et al., *Nucleic Acids Res.* 14:3167-3179, 1986). Expression of the IL-1 beta gene is also induced by these agents (Huang, J. J., et al., *J. Immunol.* 140:3838-3843, 1988). Transforming Growth Factor (TGF) alpha gene encodes a protein that can induce selfexpression. Expression of the TGF alpha gene is also induced by by IFN-gamma (Iris, F., et. al., *Nature Genetics* 3:13-145, 1993). Tumor Necrosis Factor (TNF) alpha gene encodes a protein induced by IFN gamma and IL-1 alpha (Nickoloff, B. J., et al., *J. Invest. Dermatol.* 94:151S-157S, 1990; Semon, D., et al., *Nucleic Acids Res.* 15:9083-9084, 1987), the disclosure of which is herein incorporated by reference. Granulocyte Colony Stimulating Factor (G-CSF) gene encodes a protein whose expression is induced by PMA, endotoxin, and interferons (Luger, T. A., et al., *J. Invest. Dermatol.* 95:100S-104S, 1990; Nagata, S., et al., *EMBO J.* 5:575-581, 1986). Induction of expression of the granulocyte macrophage colony stimulating factor (GM-CSF) gene occurs in response to the same stimuli as G-CSF (Luger, T. A., et al., *J. Invest. Dermatol.* 95: 100S-104S, 1990; Miyatake, S. et al., *EMBO J.* 4:2561-2568, 1985)., the disclosure of which is herein incorporated by reference. Expression of the IL-3 gene is induced by interferon (IFN) gamma, PMA, and UVB irradiation (Luger, T. A., et al., *J. Invest. Dermatol.* 95:100S-104S, 1990; Cohen, D. R., et al., *Nucl. Acids Res.* 14:3641-3658, 1986). Expression of the IL-6 gene is induced in response to other cytokines, bacterial toxins, viruses, tumor promoters and sodium lauryl sulphate (SDS) (Hunziker, T., et al., *Brit. J. Dermatol.* 127: 254-257, 1992; Luger, T. A., et al., *J. Invest. Dermatol.* 95: 100S-104S, 1990; Yasukawa, R., et al., EMBO J. 6:2939-2945, 1987). Expression of the IL-8 gene is induced by IL-1 alpha, tumor necrosis factor (TNF-alpha), and IFN-gamma. Expression of the gene can also be induced by lipopolysaccharides (LPS) and tumor promoters (Oliveira, I. C., et al., *Proc. Natl. Acad. Sci. USA* 89:9049-9053, 1992; Mukaida, N., et al., *J. Immunol.* 143:1366-1371, 1989). Expression of IL-10 is induced by contact allergens and haptens (Kim, J. M., et al., *J. Immunol.* 148:3618-3623, 1992). Expression of the Intracellular Adhesion Molecule (ICAM)-1 gene is induced by cytokines, hydrocortisone, LPS, and PMA (Caughman, S. W., et al., *J. Invest. Dermatol.* 98:61S-65S, 1992; Stade, B. G., et al., *Immunobiology* 181:851-856, 199).

3.1.1.5 Control Elements of Stress-Related Genes Associated with Cellular Energy Stresses Cellular energy stresses include conditions which affect ATP levels in the cell or cell membrane ionic gradients. Examples of energy stress include disruptions of electron transport, forced anaerobic metabolism in the presence of oxygen, depolarization of cell membranes, exposure to uncoupling agents, osmotic shock, exposure to ions (for example, calcium or sodium), and exposure to ethanol.

Control elements associated with genes that respond to cellular energy stress can be obtained from a variety of genes including, but not limited to, GRP78, FOS, TH, DBH, and ODC. GRP78 (described above), includes an energy or ionic stress responsive element which is responsive to calcium ionophores. CRE is the cAMP response element which responds to increased levels of cAMP—FOS (described above) contains the cAMP response element ("CRE") (Roesler, W. J., et al., *J. Biol. Chem.* 263:9063-9066, 1988). TH, which encodes tyrosine hydroxylase (Lamouroux, A., et al., *EMBO J.* 6:3921-3937, 1987), and DBH, which encodes dopamine beta -hydroxylase (Grima, B., *Nature* 326:707-711, 1987) are both induced by membrane depolarization. ODC encodes ornithine decarboxylase and expression of the gene is induced by osmotic shock (Hickok, N. J., et al., *DNA* 6:179-187, 1987).

3.1.2 Control Elements Derived from Genes Involved in Biochemical Pathways As described above, the control elements useful in the practice of the invention can be derived genes whose polypeptide product is known to be involved in a particular biochemical pathway. Many genes involved in biochemical pathways have been identified, sequenced and analyzed. Thus, when a control element from a gene involved in a biochemical pathway of interest is operably linked to a sequence encoding a light generating protein (e.g., a polypeptide encoding a luciferase), the effects of an analyte on expression of the gene in the pathway of interest can be monitored.

In addition, expression of multiple genes in a pathway can be monitored, for example, (1) by operably linking each selected control element to a reporter gene and introducing the expression cassettes into different animals, or (2) by operably linking each selected control element to light generating proteins (such as luciferases) which emit light at differing wavelengths. The effect of the analyte, for example where in the pathway it is acting, can be determined in this manner (e.g., via molecular epistatis).

Non-limiting examples of biochemical pathways of interest include: pathways for production of endocrines; pathways for production of prostaglandins; fatty acid and/or lipid biosynthesis pathways; pathways for production of sterol compounds (e.g., testosterone and estrogen); drug metabolism pathways, including biochemical reactions involved in enzymatic modifications of proteins. For instance, the gene encoding cytochrome P450 has been shown to be involved in drug metabolism. Thus, the control elements derived from the P450 gene can be used to construct expression cassettes for monitoring drug metabolism in vivo. Similarly, control elements derived from the genes encoding products involved in nitric oxide (NO) pathways are also useful in construction of expression cassettes that can be used to evaluate drug metabolism. Control elements derived from genes involved in N-acetylation and \S-methylation are also contemplated for use in development of test systems of drug metabolism.

Other useful genes from which regulatory (or control) elements may be obtained include the ataxia-telangiectasia (ATM) gene product, HO, and the superoxide dismutase (SOD) gene product, both of which have also been shown to play a role in oxidative damage.

In one aspect of the present invention, a single step of a biochemical pathway can be labeled. This allows analysis of individual gene expression events (e.g., induction or repression).

In a second aspect of the present invention, multiple steps within a linear pathway can be labeled (e.g., by creating reporter expression cassettes having regulatory elements derived from multiple genes in the pathway operably linked to, for example, coding sequences for a light generating protein). In this embodiment a single mouse may carry multiple expression cassettes or a cohort of mice may each carry at least one of the expression cassettes provided for labeling the selected pathway. Accordingly, single mice and cohorts of mice can be arranged into groups representing defined pathways. In the case of a single mouse, the different expression cassettes may encode, for example, coding sequences for light generating proteins that emit light at different wavelengths B thus allowing for analysis of expression mediated by different regulatory sequences within the same mouse. This aspect of the invention allows the determination of exactly what step or steps in the pathway a compound (that is being tested in the transgenic animals) is affecting (i.e., molecular epistasis analysis). Transgenic animals carrying expression cassettes labeling a pathway in such a fashion allow image analysis of the whole animal (for example to identify specific tissues that are being affected within the animal, e.g., the spleen), analysis of downstream effects, quantitation, pharmacokinetics, and possible developmental effects.

In yet a third aspect of the present invention, many genes in multi-branched pathways, branched pathways with interactions, or related pathways can be labeled using control elements derived from genes at varying points in these pathways where the control elements are used to construct reporter expression cassettes (e.g., using sequences encoding a light generating protein or light generating proteins that emit at various wavelengths). As described above, such multiple expression cassettes can be carried in single transgenic animals, as well as, employing cohorts of transgenic animals. In addition to the analyses described above, such multi-pathway labeling also allows analysis of pathway interactions and pathway redundancies.

3.1.3 Control Elements Derived from Apoptosis-Related Genes

Apoptosis in the general term for the process of programmed cell death. For a general review see, Apoptosis: the Molecular Basis of Cell Death, Tomei and Cope, eds., Current Communications in Cell and Molecular Biology 3, Cold Spring Harbor Laboratory Press, New York, 1991. Under normal conditions, apoptosis assures that the number of dying cells in a tissue is roughly equivalent to the number of newly produced cells. However, in various disease states or as a result of an insult to a tissue, dysregulation of the process of apoptosis can occur. For example, there is evidence that the excessive cell death occurs apoptosis in spinal cord injury, where the severing of axons deprives neurons of neurotrophic factors necessary to sustain cellular viability; after stroke, where after an initial phase of necrotic cell death due to ischemia, the rupture of dead cells releases excitatory neurotransmitters such as glutamate and oxygen free radicals that stimulate apoptosis in neighboring healthy neurons; and in Human Immunodeficiency Virus (HIV) infection, which induces apoptosis of T-lymphocytes.

In contrast, normal apoptosis appears to be inhibited in hyperproliferative cells, such as cancer cells. These cells tend to survive longer than their normal counterparts and, as a result, the mass of a tumor can increase even if the doubling time of the cancer cells does not increase. Genes which have been shown to play a crucial role in apoptosis include, genes encoding proteins such as Bcl-2 and a Bcl-2-related protein, termed "Bax." Specifically, the expression of Bcl-2 in a cell blocks apoptosis, whereas the expression of Bax in a cell induces apoptosis. The gene encoding the p53 tumor suppressor protein (p53) is another example of a gene that is involved apoptosis. (see, e.g., Levine, A. J. et al (1991) Nature 351: 453-455, Vogelstein, B. and Kinzler, K. W. (1992) Cell 70:523-526, Zambetti, G., and Levine, A. J. (1993) FASEB J. 7:855-865, for reviews of p53 gene). The wild-type p53 protein induces apoptosis in a cell, whereas mutant p53 proteins do not. Other genes involved in apoptosis are FAS (Itoh et al (1991) Cell 66, 233-243); interleukin-1b converting enzyme (ICE) (Miura M, Zhu H, Rotello R, Hartweig E A, Yuan J (1994) Cell 75:653-66); phosphoinositide-3-kinases (PI3Ks); serine/threonine kinase Akt/protein kinase B (PKB); BAD (Craddock, B. L., et al., J Biol Chem. 1999 Apr. 9, 274(15):10633-4); and the caspases genes.

Control elements obtained from genes involved in apoptosis are operably linked to a reporter gene, particular light generating protein (e.g., a polypeptide encoding a luciferase). In a suitable vector, the expression cassette can be introduced into cell or can be used to create transgenic animals for in vivo monitoring of gene expression of apoptosis-related genes.

3.1.4 Control Elements Derived from Genes Involved in Angiogenesis

Angiogenesis is the development of new blood vessels from existing capillaries. Aberrant expression of genes involved in angiogenesis has been implicated in a number of human diseases, as well as in the growth and metastasis of solid tumors. In some forms of arthritis, new capillaries form in the joint, leading to its gradual destruction. Solid tumors also must stimulate the formation of new blood vessels in order to obtain the nutrients and oxygen necessary for their growth, thus providing a route by which the tumors can metastasize to distant sites.

Genes products involved in angiogenesis include, acidic fibroblast growth factor (aFGF), basic fibroblast growth factor (bFGF), vascular endothelial growth factor (VEGF), platelet derived growth factor (PDGF), and transforming growth factor (TGF). (See, for example, Liotta et al., 1991, Cell 64: 327-336; Hanahan et al., Cell 86: 353-364). Other genes involved in angiogenesis are ApoB100; CETP; and sPLA2.

VEGF and VEGFR genes are discussed in greater detail below.

3.1.5 Control Elements Derived from Genes Involved in Inflammation and/or Pain Responses Transgenic animals created using the expression cassettes of the present invention will likely allow the study of pain at the level of the gene. The transgenic animals of the present invention can be used to monitor expression mediated by regulatory elements of genes involved in inflammation and/or pain responses (for example, whether reporter genes associated with such regulatory elements are overexpressed, underexpressed, or not expressed under appropriate conditions—for example, there are numerous models of pain in mice including nociceptive or analgesic sensitivity). A variety of genes that are affected by pain have been identified, for example, in mice including but not limited to the genes related to the following: neurotrophins and their receptors, peripheral mediators of nociception and hyperalgesia, opioids and their receptors, non-opioid transmitter receptors, and intracellular molecules participating in signal transduction.

Exemplary genes involved in pain responses include, but are not limited to, the gene encoding the mu opiate receptor (Uhl, G. R., et al., Proc. Nat. Acad. Sci. USA 96(14):7752-5, 1999) and the gene encoding pain modulatory neuropeptides NPFF, NPAF, and NPSF (Vilim, F. S., et al., Mol. Pharmacol. 55(5):804-11, 1999). Also, the transgenic animals of the present invention offer means for target validation in pain models. For example, evaluating expression of a reporter expression cassette where expression is mediated by mu opiate receptor (and varients thereof operably linked to, for example, a light generating protein) under conditions of a mouse model of nociception.

Expression of inflammation-related genes can also be evaluated under a variety of conditions using the reporter expression cassettes (and transgenic animals) of the present invention. Expression control sequences can be derived from the following non-limiting examples of genes: TNF; IL-2; NFKB; NFAT; INF alphalbeta; iNOS; inducible cyclooxygenase isoform COX-2 (Yang, T., et al., Am. J. Physiol. 277(1 Pt. 2):F10-6, 1999); IL-1-beta (Zhou, H. R., et al., *J. Toxicol. Environ. Health* 57(2): 115-36, 1999); TGF-beta-1 (Engle, S. J., et al., Cancer Res. 59(14):3379-86, 1999); transforming growth factor alpha, and heparin-binding epidermal growth factor (HB-EGF) (Madtes, D. K., et al., Am. J. Respir. Cell Mol. Biol. 20(5):924-34, 1999).

The COX2 gene encodes a cyclooxygenase and is a key regulator of prostaglandin synthesis. (Hla et al. (1992) *PNAS USA* 89:7384-7388; Jones et al. (1993) *J. Biol. Chem.* 268: 9049-9054). In particular, COX2 is generally considered to be a mediator of inflammation and overexpression of COX2 in rat epithelial cells results in elevated levels of E-cadherin and Bcl2. (Tsujii & DuBois (1995) *Cell* 83:493-501). In co-cultures of endothelial cells and colon carcinoma cells, cells that overexpress COX2 produce prostaglandins, proangiogenic factors and stimulate both endothelial migration and tube formation. (Tsujii et al. (1998) *Cell* 93:705-716). Experiments conducted using APC knock-out mice have demonstrated that animals homozygous for a disrupted COX2 locus develop significantly more adenomatous polyps. (Oshima et al. (1996) *Cell* 87:803-809). COX-2 knock out mice develop severe nephropathy, are susceptible to peritonitis, exhibit reduced arachidonic acid-induced inflammation and exhibit reduced indomethacin-induced gastric ulceration. (Morham et al. (1995) *Cell* 83:473-482; Langenbach et al. (1995) *Cell* 83:483-492). Female mice that are deficient in cyclooxygenase 2 exhibit multiple reproductive failures. (Lim et al. (1997) *Cell* 91:197-208.

Further, the transgenic animals of the present invention can be used to display arrays of genes that are differentially expressed under various stimuli (wherein the regulatory sequences of such genes are operably linked to sequences encoding light generating proteins). One example of a way to identify regulatory elements of genes that differential respond to a stimuli, for example inflammation, is by use of differential display RT-PCR (DDRT-PCR; see, for example, Silva, A. M., et al., Braz. J. Med. Biol. Res. 32(7):845-52, 1999; Miele G, et al., Prep Biochem Biotechnol. 1999 August;29(3):245-55; Krohn K, Glia. 1999 Feb. 15;25(4): 332-42; de Olivera JG, et al., Mol Biotechnol. 1999 April; 11(2): 195-7; Colonna-Romano S, et al., Microb Pathog. 1998 August;25(2):55-66; Smith NR, et al., *Nucleic Acids Res.* 1997 September 1;25(17):3552-4 ; Smith NR, et al., Biotechniques. 1997 August;23(2):274-9; Bhattacharjee A, et al., Biotechniques. 1997 June;22(6):1048-51; Rohde M, et al., Methods Mol Biol. 1997;67:419-30; Bauer D, et al., PCR Methods Appl. 1994 October;4(2):S97-108; Bauer D, et al., *Nucleic Acids Res.* 1993 Sep. 11;21(18):4272-8).

An advantage of the present invention is that, because evaluation of expression can be carried out in whole animals, effects on expression of reporter cassettes can be examined in specific organs, tissues, etc., as well as, the overall animal.

3.1.6 Control Elements Derived from Genes Involved in Specific Diseases

Genes which are induced during specific disease states can also be used as a source for selected control elements. In virtually any non-normal state (e.g., disease state), an organism responds by increasing expression (upregulating) of certain genes. In some instances, genes involved in disease states have been identified and, accordingly, control elements from these genes can be readily obtained as described herein and operably linked to a reporter gene of interest.

In other instances, the upregulated genes can be identified and then the control elements isolated. Identification of such genes can be any method known in the art, for example in a variation of the process known as subtractive hybridization By way of example, a substractive hybridization scheme for the identification of control elements associated with genes involved in the infectious disease of chlamydia is briefly described. Typically, mRNA is isolated cells from an animal (e.g., a mouse) infected with chlamydia and cDNA is made from the mRNA by any method known in the art. The cDNA can then be screened again a normal control. The screening is performed, for example, by exposing a chip (or other solid support) containing an array of sequences from a normal control to the cDNA obtained from the infected cells. Those transcripts that are upregulated in infected cells can be readily identified. The control elements can then be obtained by using the upregulated transcripts as clones. At any point in the process, the transcripts can be identified by screening libraries for full-length clones, by sequence comparison to known genes or by using technology such as chip arrays to identify the gene. The selected control elements are then be operably linked to the reporter gene and introduced into animals. The animals can be used to screen identify substances which effect expression of these disease-induced genes.

Another method useful for the identification and isolation of genes differentially expressed during, for example, infection of an animal by an infectious agent is differential display RT-PCR (DDRT-PCR; see, for example, Silva, A. M., et al., Braz. J. Med. Biol. Res. 32(7): 845-52, 1999; and further references cited above).

Although identification of control elements is described with respect to the infectious disease chlamydia, it will apparent be to those skilled in the art that the teachings of this specification are equally applicable to other disease states with known or unknown molecular mechanisms of disease (for example, viral infection (e.g., HIV, hepatitis B, hepatitis C, influenza, etc); microbial infection (chlamydia, Streptococcus, Stapholococcus, Pneumonia, Toxoplasma, etc.); congenital disorders; developmental disorders (e.g., including disorders affecting muscular development, organ development, cardiac development, etc.); and other disease states, many of which are discussed in different sections herein).

3.1.7 Control Elements Derived from Genes Involved in Oncogenesis

Cancer (e.g., aberrant growth of cells) often results from (i) genetic alterations occurring spontaneously, (ii) from viral infection, or (iii) in response to environmental stimuli, such as, chemical carcinogens or radiation. Genes responsible for transforming a normal cell to a cancer cell are known as oncogenes. With the advent of molecular biology, large numbers of oncogenes have been identified, cloned and sequenced. In many cases, the identified oncogenes are in altered forms of one or the same native cellular genes, known as proto-oncogenes or by overproduction(overexpression) of gene products. Exemplary non-limiting embodiments of such oncogenesis related genes include the following: tumor necrosis factor; p53; VEGF; VEG-R1; VEG-R2; and heparanse.

Exemplary promoters (including expression control elements) for use in the present invention are selected such that they are functional in a cell type and/or animal into which they are being introduced. Exemplary promoters include, but are not limited to, promoters obtained from the following mouse genes: vascular endothelial growth factor (VEGF) (VEGF promoter described in U.S. Pat. No. 5,916,763; Shima et al. (1996) *J. Bio. Chem.* 271:3877-3883; sequence available on NCBI under accession number U41383); VEGFR2, also known as Flk-1, (VEGFR-2 promoter described, for example, in Rönicke et al. (1996) *Circ. Res.* 79:277-285; Patterson et al. (1995) *J. Bio. Chem.* 270:23111-23118; Kappel et al. (1999) Blood 93:4282-4292; sequence available as accession number X89777 of NCBI database); Tie2, also known as Tek (Tie2 promoter described, for example, in Fadel et al. (1998) *Biochem. J.* 338:335-343; Schlaeger et al. (1995) *Develop.* 121:1089-1098; Schlager et al. (1997) *PNAS USA* 94:3058-3063). VEGF is a specific mitogen for EC in vitro and a potent angiogenic factor in vivo. In a tumorigenesis study, it was shown that VEGF was critical for the initial subcutaneous growth of T-47D breast carcinoma cells transplanted into nude mice, whereas other angiogenic factors, such as, bFGF can compensate for the loss of VEGF after the tumors have reached a certain size (Yoshiji, H., et al.,1997 Cancer Research 57: 3924-28). VEGF is a major mediator of aberrant EC proliferation and vascular permeability in a variety of human pathologic situation, such as, tumor angiogenesis, diabetic retinopathy and rheumatoid arthritis (Benjamin L E, et al., 1997 PNAS 94: 8761-66; Soker, S., et al., 1998 Cell 92: 735-745). VEGF is synthesized by tumor cells in vivo and accumulates in nearby blood vessels. Because leaky tumor vessels initiate a cascade of events, which include plasma extravasation and which lead ultimately to angiogenesis and tumor stroma formation, VEGF plays a pivotal role in promoting tumor growth (Dvorak, H. F., et al., 1991 J Exp Med 174:1275-8). VEGF expression was upregulated by hypoxia (Shweiki, D., et al., 1992 Nature 359: 843-5). VEGF is also upregulated by overexpression of v-Src oncogene (Mukhopadhyay. D., et al., 1995 Cancer Res. 15: 6161-5), c-SRC (Mukhopadhyay, D., et al., 1995 Nature 375: 577-81), and mutant ras oncogene (Plate, K.H., et al., 1992 Nature 359: 845-8). The tumor suppressor p53 downregulates VEGF expression (Mukhopadhyay. D., et al., 1995 Cancer Res. 15: 6161-5).

Alternative names for some of these genes are as follows: VEGF (vascular endothelial growth factor)is also named VPF (vascular permeability factor); VEGFR-1 is also named FLT1; VEGFR-2 is also named KDR/FLK1; and VEGFR-3 is also named FLT4.

VEGF is a homodimeric 45 kDa (monomer 23 kDa) protein. VEGF has five isoforms of which VEGF165 and VEGF121 are the most abundant. Both are ligands for VEGFR-2 as well as VEGFR-1 (Soker, S., et al., JBC 271: 5761-67, 1996). VEGF165 is the only VEGF isoform that binds to Neuropillin-1 (Soker, S., et al., Cell 92:735-745, 1998). VEGF is extremely unstable—its half life in circulation is only 3 minutes (Ferrara, N., et al., Nature 380:439-442, 1996; Ferrara, N., et al., Endocr Rev 18:4-25, 1997).

VEGF-B is 43% (aa) identical to VEGF and exists as homodimers. It can also form heterodimers with VEGF (Olofsson, B., et al., Proc Natl Acad Sci USA 93:2576-81, 1996). VEGF-B is a ligand for VEGFR-1 (Olofsson, B., et al., Proc Natl Acad Sci USA 95:11709-14, 1998).

VEGF-C is 30% (aa) identical to VEGF. The mature VEGF-C is 23 kDa, the precursor protein is 35.8 kDa. VEGF-C is a ligand for VEGFR-3 as well as VEGFR-2. It induces autophosphorylation of both receptors (Joukov, V., et al., EMBO J 15:290-298, 1996).

VEGF-D is 31% (aa) identical to VEGF165 and 48% (aa) identical to VEGF-B. The mature VEGF-D is approximately 22 KDa. VEGF-D is a ligand for VEGFR-3 as well as VEGFR-2. It induces autophosphorylation of both receptors (Achen, M. G., et al., 1998 Proc Natl Acad Sci USA 95:548-53, 1998).

PIGF is 46% identical (aa) to VEGF (Maglione, D., et al., Proc Natl Acad Sci 88:9267-71, 1991) and can form heterodimers with VEGF ((Disalvo, J., et al., JBC 270:7717-23, 1995).

VEGFR-1 is an approximately 180 KDa tyrosine kinase receptor for VEGF-B (Olofsson, B., et al., Proc Natl Acad Sci USA 95:11709-14, 1998) and VEGF (de Vries, C., et al., Science 255:989-91, 1992) and PIGF (Park, J. E., et al., J Biol Chem 269:25646-54, 1994).

VEGFR-2 is an approximately 200 KDa tyrosine kinase receptor for VEGF (Terman, B. I., et al., Oncogene September 6(9):1677-83, 1991), VEGF-C (Joukov, V., et al., EMBO J 15:290-298, 1996), and VEGF-D (Achen, M. G., et al., 1998 Proc Natl Acad Sci USA 95:548-53, 1998).

VEGFR-3 is a tyrosine kinase receptor (Pajusola, K., et al., Cancer Res 52:5738-43, 1992) on lymphatic EC for VEGF-C (Dumont, D. J., et al., Science 282:946-949, 1998) and VEGF-D (Achen, M. G., et al., 1998 Proc Natl Acad Sci USA 95:548-53, 1998). VEGFR-3 has a processed mature form of about 125 kDa, and an unprocessed form of about 195 kDa (Achen, M. G., et al., 1998 Proc Natl Acad Sci USA 95:548-53, 1998).

Neuropillin-1 is an approximately 130 KDa receptor tyrosine kinase. It binds VEGF165, but not VEGF121 (Soker, S., et al., Cell 92:735-745, 1998).

Expression of many of these genes has been evaluated in adults. A summary of information relating to expression follows here.

VEGF has an approximately 3.7 kb transcript. It is expressed in multiple human tissues, including heart, skeletal muscle and prostate. In mouse, VEGF is mainly expressed in heart, lung and kidney. The rest of the human or mouse tissues, including brain and testis, do not express detectable or significant level of VEGF (Olofsson, B., et al., Proc Natl Acad Sci USA 93:2576-81, 1996). In another study, it was shown that VEGF is highly expressed in epithelial cells of lung alveoli, renal glomeruli and adrenal cortex and in cardiac myocytes (Berse, B., MCB 3:211-20, 1992).

VEGF-B has an approximately 1.4 kb transcript. It is expressed in a majority of human and mouse tissues. In human, VEGF-B is most prominently expressed in heart, skeletal muscle, pancreas, brain and prostate. In mouse, VEGF-B is mostly expressed heart, skeletal muscle, brain and kidney. Liver does not appear to express a significant level of VEGF-B in either humans or mice. VEGF-B and VEGF are co-expressed in many human tissues, such as heart, skeletal muscle, pancreas and prostate. In general, VEGF-B is more abundantly expressed than VEGF. VEGF-B can act as an endothelial cell growth factor (Olofsson, B., et al., Proc Natl Acad Sci USA 93:2576-81, 1996).

VEGF-C has an approximately 2.4 kb transcript that is expressed in multiple human tissues, most prominently in heart, skeletal muscle, placenta, ovary, small intestine, pancreas and prostate. Several tissues, including brain and liver, do not appear to express detectable levels of VEGF-C (Joukov, V., et al., EMBO J 15:290-298, 1996).

VEGF-D has an approximately 2.3 kb transcript that is expressed in multiple human tissues, most prominently in heart, skeletal muscle, lung, colon and small intestine. Several tissues, including brain, liver, placenta, do not appear to express detectable levels of VEGF-D (Achen, M. G., et al., 1998 Proc Natl Acad Sci USA 95:548-53, 1998).

VEGFR-1 appears to be endothelial cell specific (Peters, K. G., et al., Proc Natl Acad Sci 90:8915-19, 1993). VEGFR-1 cDNA is approximately 7.7 kb and encodes a protein of 1338 aa. It was expressed in a variety of normal tissues of adult rat (Shibuya, M., et al., Oncogene 5:519-24, 1990). In a glioma model of tumor angiogenesis, both VEGFR-1 and VEGFR-2 are specifically expressed in Ecs that have penetrated into the tumor, but are absent from Ecs in the normal brain tissues. VEGF expression was detectable in glioma cells along necrotic edge (Plate, K. H., et al., Cancer Research 53:5822-27, 1993).

VEGFR-2 is expressed as an approximately 7 kb transcript (Terman, B. I., et al., Oncogene September 6(9):1677-83, 1991) that appears to be endothelial cell specific. VEGFR-2 is expressed ubiquitously in many tissues, including heart, placenta, lung and kidney. The expression levels of VEGFR-2 are relatively low in these tissues compared with neuropillin expression. Brain does not appear to express detectable levels of VEGFR-2 (Soker, S., et al., Cell 92:735-745, 1998). In situ hybridization analysis revealed a specific association of VEGFR-2 with endothelial cells at all stages of mouse development. It is abundant in proliferating endothelial cells of vascular sprouts and branching vessels of embryonic and early postnatal brain, but were drastically reduced in adult brain, where proliferation has ceased (Millauer, B., Cell 72:835-46, 1993).

VEGFR-3 is expressed as approximately 5.8 kb and 4.5 kb mRNAs. Most fetal tissues expressed VEGFR-3, with spleen, brain intermediate zone, and lung showing the highest levels. It does not appear to be expressed in the endothelial cells of blood vessels (Pajusola, K., et al., Cancer Res 52:5738-43, 1992). During embryonic development, VEGFR-3 is expressed in blood vessels but become largely restricted to the lymphatic endothelium postnatally (Kaipainen, A., et al., Proc Natl Acad Sci USA 92: 3566-3570, 1995).

Neuropillin-1 is expressed in both endothelial cells and many types of tumor cells as an approximately 7 kb transcript. Most tissues express high level of Neuropillin-1, especially in heart and placenta. Skeletal muscle, pancreas, lung and kidney also express high level of Neuropillin-1. Brain does not appear to express detectable levels of Neuropillin-1 (Soker, S., et al., Cell 92:735-745, 1998).

Some functions of these genes have been evaluated and are as follows.

VEGF is a specific mitogen for EC in vitro and a potent angiogenic factor in vivo. In vitro, VEGF binds and induces autophosphorylation of VEGFR-2 and VEGFR-1, but the mitogenic response is mediated only through VEGFR-2 (Waltenberger, J., JBC 269:26988-95, 1994). VEGF functions as a survival factor for newly formed vessels during developmental neovascularization, possibly through mediating interaction of endothelial cells with underlying matrix, but is not required for maintenance of mature vessels (Benjamin, L. E., et al., Proc Natl Acad Sci 94:8761-66, 1997). In embryogenesis, VEGF and VEGFR-2 interaction induces the birth and proliferation of endothelials (Hanahan, D., Science 277:48-50, 1997). Binding of VEGF to VEGFR-2 elicits endothelial cell-cell interactions and capillary tube formation, a process that follows closely proliferation and migration of endothelial cells (Hanahan, D., Science 277:48-50, 1997). In a tumorigenesis study, it was shown that VEGF is critical for the initial s.c. growth of T-47D breast carcinoma cells transplanted into nude mice, whereas other angiogenic factors such as bFGF can compensate for the loss of VEGF after the tumors have reached a certain size (Yoshiji, H., et al., Cancer Research 57:3924-28, 1997). VEGF is a major mediator of aberrant endothelial cells (EC) proliferation and vascular permeability in a variety of human pathologic situation, such as tumor angiogenesis, diabetic retinopathy and rheumatoid arthritis (Benjamin, L. E., et al., Proc Natl Acad Sci 94:8761-66, 1997, Soker, S., et al., Cell 92:735-745, 1998). VEGF induces expression of plasminogen activator (PA), PA inhibitor 1 (PAI-1), MMP, and interstitial collagenase in EC. These findings are consistent with the proangiogenic activities of VEGF. VEGF promotes expression of VCAM-1 and ICAM-1 in EC, thus may facilitate the adhesion of activated NK cells to EC. VEGF may promote monocyte chemotaxis (Pepper, M. S., et al., BBRC 181:902-906, 1991; Ferrara, N., et al., Endocr Rev 18:4-25, 1997). Tumors are believed to be the principal source of VEGF. A correlation has been observed between VEGF expression and vessel density in human breast tumors, renal cell carcinoma and colon cancer (Fong, T. A. T., et al., Cancer Res 59:99-106, 1999). VEGF and PGF expressions were significantly upregulated in 96% and 91% of hypervascular renal carcinoma tissues compared with adjacent normal kidney tissues (Takahashi, A., et al., Cancer Res 54:4233-7, 1994).

VEGF-B is a mitogen for EC and may be involved in angiogenesis in muscle and heart (Olofsson, B., et al., Proc Natl Acad Sci USA 93:2576-81, 1996). In vitro, binding of VEGF-B to its receptor VEGFR-1 leads to increased expression and activity of urokinase-type plasminogen activator and plasminogen activator inhibitor, suggesting a role for VEGF-B in the regulation of extracellular matrix degradation, cell adhesion, and migration (Olofsson, B., et al., Proc Natl Acad Sci USA 95:11709-14, 1998).

VEGF-C may regulate angiogenesis of lymphatic vasculature, as suggested by the pattern of VEGF-C expression in mouse embryos (Kukk, E., et al., Development 122:3829-37, 1996). Although VEGF-C is also a ligand for VEGFR-2, the functional significance of this potential interaction is unknown. Overexpression of VEGF-C in the skin of transgenic mice resulted in lymphatic, but not vascular, endothelial proliferation and vessel enlargement, suggesting the major function of VEGF-C is through VEGFR-3 rather than VEGFR-2 (Jeltsch, M., et al., Science 276:1423-5, 1997). Using the CAM assay, VEGF and VEGF-C were shown to be specific angiogenic and lymphangiogenic growth factors, respectively (Oh, S. J., et al., Del Biol 188:96-109, 1997).

VEGF-D is a mitogen for EC. VEGF-D can also activate VEGFR-3. It is possible that VEGF-D could be involved in the regulation of growth and/or differentiation of lymphatic endothelium (Achen, M. G., et al., 1998 Proc Natl Acad Sci USA 95:548-53, 1998).

PlGF can potentiate the action of low concentrations of VEGF in vitro and in vivo (Park, J. E., et al., J Biol Chem 269:25646-54, 1994).

VEGFR-1 signaling pathway may regulate normal endothelial cell-cell or cell-matrix interactions during vascular development, as suggested by a knockout study (Fong, G. H., et al., Nature 376:65-69, 1995). Although VEGFR-1 has a higher affinity to VEGF than VEGFR-2, it does not transduce the mitogenic signals of VEGF in ECs (Soker, S., et al., Cell 92:735-745, 1998).

VEGFR-2 appears to be the major transducer of VEGF signals in EC that result in chemotaxis, mitogenicity and gross morphological changes in target cells (Soker, S., et al., Cell 92:735-745, 1998).

VEGFR-3 has an essential role in the development of the embryonic cardiovascular system before the emergence of lymphatic vessels, as shown by a knockout study (Dumont, D. J., et al., Science 282:946-949, 1998).

Neuropillin-1 is a receptor for VEGF165. It can enhance the binding of VEGF165 to VEGFR-2 and VEGF165 mediated chemotaxis (Soker, S., et al., Cell 92:735-745, 1998).

Gene regulation of some of these genes has been investigated and is discussed herein below.

In situ hybridization demonstrated VEGF mRNA was present in transplanted tumor cells but not in tumor blood vessels, indicating that immunohistochemical labeling of tumor vessels with VEGF antibodies reflects uptake of VEGF, not endogenous synthesis. VEGF protein staining was evident in adjacent preexisting venules and small veins as early as 5 hours after tumor transplant and plateaued at maximally intense levels in newly induced tumor vessels by approximately 5 days. In contrast, vessels more than approximately 0.5 mm distant from tumors were not hyperpermeable and did not exhibit immunohistochemical staining for VEGF. Vessel staining disappeared within 24-48 hours of tumor rejection. These studies indicate that VEGF is synthesized by tumor cells in vivo and accumulates in nearby blood vessels. Because leaky tumor vessels initiate a cascade of events, which include plasma extravasation and which lead ultimately to angiogenesis and tumor stroma formation, VEGF plays a pivotal role in promoting tumor growth (Dvorak, H. F., et al., J Exp Med 174:1275-8, 1991). In addition, it was shown that stromal cells can be stimulated by transplanted tumor cells for VEGF production (Fukumura, D., et al., Cell , 94:715-25, 1998). Fibroblasts cultured in vitro are highly activating for VEGF promoter function compared with fibroblasts in freshly isolated tumors, indicating the culture condition did not mimic the status of normal (unactivated) tissue in vivo (Fukumura, D., et al., Cell, 94:715-25, 1998). For example, C6 tumor spheroids (C6 is a cell line derived from a rat glial tumor—C6 cells aggregate and form small spheroids in culture) implanted into nude mice became neovascularized accompanied by a gradual reduction of VEGF expression (Shweiki, D., et al., Proc Natl Acad Sci 92:768-772, 1995). The VEGF promoter region bears many of the characteristics of a house-keeping gene (Tischer, E., JBC 266:1194-11954, 1991), hence it is likely that almost any cell type could serve as a source for VEGF upon hypoxic or ischemic demand (Fukumura, D., et al., Cell, 94:715-25, 1998).

VEGF expression was upregulated by hypoxia (Shweiki, D., et al., Nature 359:843-5, 1992), due to both increased transcriptional activation and stability of its mRNA (Ikeda, E., et al., JBC 270:19761-5, 1995). In a number of in vitro studies, it was shown that hypoxia upregulates VEGF expression through the activation of PI3K/Akt pathway (Mazure, N. M., et al., Blood 90:3322-31, 1997) and HIF-1 (an enhancer induced by hypoxia and bind to VEGF promoter region) (Forsythe, J. A., MCB 16:4604-13, 1996; Mazure, N. M., et al., Blood 90:3322-31, 1997). VEGF is also upregulated by overexpression of v-Src oncogene (Mukhopadhyay, D., Cancer Res. 15:6161-5, 1995), c-SRC (Mukhopadhyay, D., et al., Nature 375:577-81, 1995), and mutant ras oncogene (Plate, K. H., Nature 359:845-8, 1992). The tumor suppressor p53 downregulates VEGF expression (Mukhopadhyay, D., Cancer Res. 15:6161-5, 1995). A number of cytokines and growth factors, including PGF, TPA (Grugel, S., et al., JBC 270: 25915-9, 1995), EGF, TGF-b, IL-1, and IL-6 induce VEGF mRNA expression in certain type of cells (Ferrara, N., et al., Endocr Rev 18:4-25, 1997). Kaposi's sarcoma-associated herpesvirus (KSHV), which encodes a G-protein-coupled receptor—a homolog of IL-8 receptor, can activate JNK/SAPK and p38MAPK and increase VEGF production, thus causing cell transformation and tumorigenicity. (Bais, C., Nature 391:86-9, 1998).

The growth of androgen-dependent Shionogi carcinoma in immunodeficient mice was regressed after the mice were castrated, accompanied by decrease in VEGF expression. Two weeks after castration, a second wave of angiogenesis and tumor growth begins with a concomitant increase in VEGF expression. (Jain, R. K., Proc Natl Acad Sci USA 95:10820-5, 1998).

VEGF-D is induced by transcription factor c-fos in mouse (Orlandini, M. Proc Natl Acad Sci 93:11675-80, 1996).

Overexpression of some of these genes has been evaluated using different systems.

VEGF overexpression in skin of transgenic mice induces angiogenesis, vascularhyperpermeability and accelerated tumor development (Larcher, F., et al., Oncogene 17:303-11, 1998). Retina tissue-specific VEGF overexpression in transgenic mice cause intraretinal and subretinal neovascularization (Okamoto, N., et al., Am J Pathol 151:281-91, 1997). VEGF overexpression mediated by the Tet system promotes tumorigenesis of C6 glioma cells when transplanted into nude mice. The tumors become hypervascularized with abnormally large vessels, arising from excessive fusions. The tumors were less necrotic. After VEGF expression was shut off, regression of the tumors occurred due to detachment of endothelial cells from the walls of preformed vessels and their subsequent apoptosis. Vascular collapse further lead to hemorrhages and extensive tumor necrosis (Benjamin, L. E., et al., Proc Natl Acad Sci 94:8761-66, 1997). In human-VEGF-promoter-GFP transgenic mice, implantation of solid tumor induces specific GFP expression in stromal cells. Transgenic mice were mated with Tantigen mice (able to form spontaneous mammary tumors) to generate double transgenic mice, in which spontaneous mammary tumors were formed. Strong stromal, but not tumor, expression of GFP was observed (Fukumura, D., et al., Cell, 94:715-25, 1998). A CCD camera was used to monitor GFP expression. GFP half life was shown to be between about 1.2-1.5 days (Fukumura, D., et al., Cell, 94:715-25, 1998). The transgene was integrated into the IgG locus of the chromosome through DNA recombination (Fukumura, D., et al., Cell, 94:715-25, 1998). FVB derived VEGF-GFP transgenic mice were mated with wild-type C3H mice to create hybrid mice that can be served as hosts for C3H derived tumor lines (Fukumura, D., et al., Cell, 94:715-25, 1998).

VEGF-C overexpression in the skin of transgenic mice resulted in lymphatic, but not vascular, endothelial proliferation and vessel enlargement (Jeltsch, M., et al., Science 276: 1423-5, 1997).

Neuropillin-1 overexpression in transgenic mice resulted in embryonic lethality. The embryos possessed excess capillaries and blood vessels. Dilated vessels and hemorrhage were also observed (Kitsukawa, T., et al., Development 121: 4309-18, 1995).

The functions of some of these genes have been evaluated in knock-out mice constructs, animal studies, and in vitro studies.

A VEGF knockout was an embryonic lethal. F1 is also embryonic lethal and angiogenesis was impaired. VEGF secretion from +/− ES cells was reduced to 50% (Carmellet, P., et al., *Nature* 380:435-439, 1996; Ferrara, N., et al., Nature 380:439-442, 1996).

VEGFR-1 was evaluated in a lacZ knock-in wherein a fragment of the exon that contains ATG start codon was replaced by LacZ. Knockout mice were embryonic lethal. Blood vessels were formed, but the organization of the blood vessel was perturbed (Fong, G. H., et al., Nature 376:65-69, 1995).

VEGFR-2 was an embryonic lethal caused by defective endothelial cell development (Shalaby, F., et al., Nature 376: 62-65, 1995).

VEGFR-3(LacZ Knock-in) was an embryonic lethal caused by defective blood vessel development (Dumont, D. J., et al., Science 282:946-949, 1998).

Neuropillin-1 was an embryonic lethal (Dumont, D. J., et al., Science 282:946-949, 1998).

In vitro studies showed that a mutant VEGF (a heterodimer of two mutant VEGF) (Siemeister, G., et al., Proc Natl Acad Sci 95:4625-9, 1998), as well as a GST-Exon7 (VEGF) fusion protein (Soker, S., et al., JBC 272:31582-88, 1997), was able to inhibit endothelial cell proliferation by acting as an VEGF antagonist and interfering VEGF binding to VEGFR-2 and VEGFR-1 (Siemeister, G., et al., Proc Natl Acad Sci 95:4625-9, 1998). More importantly, A VEGF neutralizing chimeric protein, containing the extracellular domain of VEGF receptor (either VEGFR-1 or VEGFR-2) fused with IgG, substantially reduced the development of retinal neovascularization when injected into mice with ischemic retinal disease (Aiello, L. P., et al., Proc Natl Acad Sci 92:10457-61, 1995).

Treatment of tumors with monoclonal antibodies directed against VEGF resulted in dramatic reduction in tumor mass due to the suppression of tumor angiogenesis (Kim, K. J., et al., Nature 362:841-44, 1993). Injection of antibodies against VEGF reduced tumor vascular permeability and vessel diameter in immunodeficient mice transplanted with human glioblastoma, colon adenocarcinoma, and melanoma (Yuan, F., et al., Proc Natl Acad Sci 93:14765-70, 1996). Retrovirus mediated overexpression of a dominant negative form of VEGFR-2 in nude mice suppresses the growth of transplanted rat C6 glioma tumor cells (Millauer, B., et al., Nature 367: 576-9, 1994) mammary, ovarian tumors and lung carcinoma (Millauer, B., et al., Cancer Res 56:1615-20, 1996).

Much of the difficulty in understanding tumor dynamics come from the complexity of the experimental systems in vivo and from the failure of in vitro culture models to faithfully reflect events taking place in an organismic context (Fukumura, D., et al., Cell, 94:715-25, 1998). Fibroblasts cultured in vitro are highly activating for VEGF promoter function compared with fibroblasts freshly isolated from tumors, indicating the culture conditions did not mimic the status of normal (unactivated) tissue in vivo (Fukumura, D., et al., Cell, 94:715-25, 1998). The constructs and methods described herein provide valuable resources for evaluating the roles of these genes in vivo, in whole animals.

As described herein, such promoters and associated expression control elements can be used to generate the expression cassettes and transgenic animals of the present invention. For example, a group of expression cassettes having control sequences derived from oncogenesisrelated genes can be used to generate a mouse or a cohort of mice useful for evaluation of the oncogenic potential of compounds (wherein the compounds can be administered to the transgenic animals and the expression of the reporter expression cassettes monitored).

3.1.8 Control Elements Dervied from Genes Involved in Development

As mentioned above, the present invention is also applicable to creating in vivo models of genes involved in different stages of development as well as genes involved in developmental disorders. Exemplary, non-limiting examples of development-associated genes include the following. The bmp-4 gene product (Katagiri T, et al., Dev Genet. 22(4):340-8, 1998) has been shown to be involved in gastrulation and mesoderm formation. The bmp5 gene product (Solloway M J, et al., Development. 126(8): 1753-68, 1999; Bailon-Plaza A, et al., Bone. 24(3):211-6, 1999) appears to be involved in skeletal defects while the bmp7 gene product (Katagiri T, et al., Dev Genet. 22(4):340-8, 1998; Solloway M J, et al., Development. 126(8):1753-68, 1999) appears to be involved in kidney, eye and skeletal development. Using the methods described herein, promoters and expression control elements associated with such genes can be used to generate expression cassettes and transgenic animals. Transgenic animals carrying such reporter expression cassettes can be used to evaluate, for example, the effect of a compound on expression of development-associated genes and may be indicative of, for example, teratogenic effects of such compounds in animals.

3.2.0 Reporter Genes Useful in the Practice of the Present Invention

Reporter genes useful in the practice of the present invention include sequences encoding light generating proteins or polypeptides. Non-limiting examples of such sequences encoding light generating proteins include both lux genes (procaryotic genes encoding a luciferase activity) and luc genes (eucaryotic genes encoding a luciferase activity). A variety of luciferase encoding genes have been identified including, but not limited to, the following: B. A. Sherf and K. V. Wood, U.S. Pat. No. 5,670,356, issued Sep. 23, 1997; Kazami, J., et al., U.S. Pat. No. 5,604,123, issued Feb. 18, 1997; S. Zenno, et al, U.S. Pat. No. 5,618,722; K. V. Wood, U.S. Pat. No. 5,650,289, issued Jul. 22, 1997; K. V. Wood, U.S. Pat. No. 5,641,641, issued Jun. 24, 1997; N. Kajiyama and E. Nakano, U.S. Pat. No. 5,229,285, issued Jul. 20, 1993; M. J. Cormier and W. W. Lorenz, U.S. Pat. No. 5,292,658, issued Mar. 8, 1994; M. J. Cormier and W. W. Lorenz, U.S. Pat. No. 5,418,155, issued May 23, 1995; de Wet, J.R., et al, *Molec. Cell. Biol.* 7:725-737, 1987; Tatsumi, H. N., et al, *Biochim. Biophys. Acta* 1131:161-165, 1992; and Wood, K. V., et al, *Science* 244:700-702, 1989; all herein incorporated by reference. Luciferase catalyzes a reaction using luciferin as a luminescent substrate to produce light. A typical excitation maxima, for detection of luciferase activity is 550 nm.

In one embodiment of the present invention, a stress-responsive control element is operably linked to a selected reporter gene. When several stress-responsive control elements are to be employed in the generation of a single transgenic animal (or line of animals), then each stress-responsive control element can be operatively linked to, for example, sequences encoding luciferases having different excitation maxima (i.e., luciferases that produce different colors of light). Such constructs allow the identification of which stress-responsive control element is being induced under a particular set of conditions. For example, Kajiyama and Nakano (*Protein Eng.* 4(6):691-693, 1991; U.S. Pat. No. 5,330,906, issued Jul. 19, 1994, herein incorporated by reference) teach five variant firefly luciferases generated by single amino acid changes to the *Luciola cruciata* luciferase coding sequence. The variants have excitation maxima of 558 nm, 595 nm, 607 nm, 609 nm and 612 nm. A typical range to examine excitation maxima in is between about 300 nm and 1100 nm.

In addition to control elements derived from genes of interest (typically including a promoter and expression control sequences), the reporter gene cassette of the present invention may also include further expression control elements, for example, transcription termination signals, polyadenylation sequences (located 3' to the translation stop codon), sequences for optimization of initiation of translation (located 5=to the coding sequence), and translation termination sequences. Further, codon usage in the coding sequences of light generating polypeptide (which is selected for use in the present invention) can be optimized to correspond to the animal in which the transgene is to be expressed (for example, mice).

4.0.0 Evaluation of Selected Control Elements in Transgenic Animals

Transgenic animals for use in the practice of the present invention can be generating by following the teachings of the present specification for the creation of reporter gene cassettes (comprising, for example, stress-responsive control elements, including a functional promoter, and a luciferase reporter gene) and the incorporation of such reporter gene cassettes into animals using established methods. Methods of generating transgenic, non-human animals are known in the art (Leder, P., et al, U.S. Pat. No. 4,736,866, issued Apr. 12, 1988; Melmed, S., et al., U.S. Pat. No. 5,824,838, issued Oct. 20, 1998; Bosch; F., et al, U.S. Pat. 5,837,875, issued, Nov. 17, 1998; Capecchi, M. R., et al, U.S. Pat. No. 5,487,992, issued Jan. 30, 1996; Bradley, A., et al, U.S. Pat. No. 5,614, 396, issued Mar. 25, 1997; Ruley, H. E., U.S. Pat. No. 5,627, 058, issued May 6, 1997; all herein incorporated by reference).

In the practice of the method of the present invention, the analyte of interest (for example, a drug that is being screened to determine its toxicity) is administered to the transgenic animal. The analyte can be administered to the transgenic animal by any standard route and may be accompanied by a pharmaceutically acceptable carrier. Methods of administration include, but are not limited to, injection (subcutaneously, epidermally, intradermally), intramucosal (such as nasal, rectal and vaginal), intraperitoneal, intravenous, oral or intramuscular. Other modes of administration include oral and pulmonary administration, suppositories, and transdermal applications. Dosage treatment may be a single dose schedule or a multiple dose schedule. For example, the analyte of interest can be administered over a range of concentration to determine a dose/response curve. The analyte may be administered to a series of test animals or to a single test animal (given that response to the analyte can be cleared from the transgenic animal).

In one aspect of the present invention, a transgenic animal or cohort of transgenic animals is prepared and supplied to an entity in need of such animals to use, for example, in screening an analyte or analytes of interest.

The substrate for the reporter gene, if one is necessary, is also administered to the transgenic animal. Appropriate concentrations for the substrate can be empirically determined for each line of test animal constructed. The substrate (typically, luciferin) can be administered before, concomitantly with, or after the administration of the analyte of interest. The routes of administration of the substrate can be as described for the analyte. Preferred routes of administration for the substrate include, but are not limited to, intravenous or topical administration.

The monitoring of expression of lux/luc reporter genes using non-invasive whole animal imaging has been described (Contag, C., et al, U.S. Pat. No. 5,650,135, Jul. 22, 1997, herein incorporated by reference; Contag, P., et al, *Nature Medicine* 4(2):245-247, 1998; Contag, C., et al, OSA TOPS on *Biomedical Optical Spectroscopy and Diagnostics* 3:220-224, 1996; Contag, C. H., et al, *Photochemistry and Photobiology* 66(4):523-531, 1997; Benaron, D. A., et al, *Phil. Trans. R. Soc. London* B 352:755-761, 1997; Contag, C. H., et al, *Molecular Microbiology* 18(4):593-603, 1995). Such imaging typically uses at least one photo detector device element, for example, a charge-coupled device (CCD) camera.

4.1.0 An Alternative Method of Generating Substantially Isogenic Transgenic Animals A novel method useful for generating substantially isogenic individual and/or cohorts of transgenic animals of the present invention is described below. The following method of generating transgenic animals employs targeting cassettes typically including the following components: (1) a suitable vector backbone; (2) a polynucleotide encoding a light generating protein; (3) a promoter operably linked to sequences encoding the light generating protein, wherein the promoter is heterologous to the light generating protein coding sequences; (4) a sequence encoding a positive selection marker; (5) insertion sites flanking the sequence encoding the positive selection marker and the polynucleotide encoding a luciferase gene, for insertion of sequences which target a single-copy, non-essential chromosomal gene; and, optionally, (6) a sequence encoding a negative selection marker.

Suitable vector backbones generally include an F1 origin of replication; a colE1 plasmid-derived origin of replication; polyadenylation sequence(s); sequences encoding antibiotic resistance (e.g., ampicillin resistance) and other regulatory or control elements. Non-limiting examples of appropriate backbones include: pBluescriptSK (Stratagene, La Jolla, Calif.); pBluescriptKS (Stratagene, La Jolla, Calif.) and other commercially available vectors.

Sequences encoding light generating proteins have been discussed above. Luciferase coding sequences useful in the practice of the present invention include sequences obtained from lux genes (procaryotic genes encoding a luciferase activity) and luc genes (eucaryotic genes encoding a luciferase activity). A variety of luciferase encoding genes have been identified including, but not limited to, the following: B. A. Sherf and K. V. Wood, U.S. Pat. No. 5,670,356, issued Sep. 23, 1997; Kazami, J., et al., U.S. Pat. No. 5,604, 123, issued Feb. 18, 1997; S. Zenno, et al, U.S. Pat. No. 5,618,722; K. V. Wood, U.S. Pat. No. 5,650,289, issued Jul. 22, 1997; K. V. Wood, U.S. Pat. No. 5,641,641, issued Jun. 24, 1997; N. Kajiyama and E. Nakano, U.S. Pat. No. 5,229,285, issued Jul. 20, 1993; M. J. Cormier and W. W. Lorenz, U.S. Pat. No. 5,292,658, issued Mar. 8, 1994; M. J. Cormier and W. W. Lorenz, U.S. Pat. No. 5,418,155, issued May 23, 1995; de Wet, J. R., et al, *Molec. Cell. Biol.* 7:725-737, 1987; Tatsumi, H. N., et al, *Biochim. Biophys. Acta* 1131:161-165, 1992; and Wood, K. V., et al, *Science* 244:700-702, 1989; all herein incorporated by reference. Eukaryotic luciferase catalyzes a reaction using luciferin as a luminescent substrate to produce light, whereas prokaryotic luciferase catalyzes a reaction using an aldehyde as a luminescent substrate to produce light.

Wild-type firefly luciferases typically have an emission maxima at about 550 nm. Numerous variants with differing emission maxima have also been studied. For example, Kajiyama and Nakano (*Protein Eng.* 4(6):691-693, 1991; U.S. Pat. No. 5,330,906, issued Jul. 19, 1994, herein incorporated by reference) teach five variant firefly luciferases generated by single amino acid changes to the Luciola cruciata luciferase coding sequence. The variants have emission peaks of 558 nm, 595 nm, 607 nm, 609 nm and 612 nm. A yellow-green luciferase with an emission peak of about 540 nm is commerically available from Promega, Madison, Wis. under the name pGL3. A red luciferase with an emission peak of about 610 nm is described, for example, in Contag et al. (1998) *Nat. Med.* 4:245-247 and Kajiyama et al. (1991) *Prot. Eng.* 4:691-693.

Positive selection markers include any gene which a product that can be readily asssayed. Examples include, but are not limited to, a hprt gene (Littlefield, J. W., Science 145:709-710 (1964), herein incorporated by reference), a xanthine-guanine phosphoribosyltransferase (gpt) gene, or an adenosine phosphoribosyltransferase (aprt) gene (Sambrook et al., supra), a thymidine kinase gene (i.e ATK@) and especially the TK gene of herpes simplex virus (Giphart-Gassler, M. et al., Mutat. Res. 214:223-232 (1989) herein incorporated by reference), a nptII gene (Thomas, K. R. et al., Cell 51:503-512 (1987); Mansour, S. L. et al., Nature 336:348-352 (1988), both references herein incorporated by reference), or other genes which confer resistance to amino acid or nucleoside analogues, or antibiotics, etc, for example, gene sequences which encode enzymes such as dihydrofolate reductase (DHFR) enzyme, adenosine deaminase (ADA), asparagine synthetase (AS), hygromycin B phosphotransferase, or a CAD enzyme (carbamyl phosphate synthetase, aspartate transcarbamylase, and dihydroorotase).

Addition of the appropriate substrate of the positive selection marker can be used to determine if the product of the positive selection marker is expressed, for example cells which do not express the positive selection marker nptII, are killed when exposed to the substrate G418 (Gibco BRL Life Technology, Gaithersburg, Md.).

The targeting vector typically contains insertion sites for inserting targeting sequences (e.g., sequences that are substantially homologous to the target sequences in the host genome where integration of the targeting vector/expression cassette is desired). These insertion sites are preferably included such that there are two sites, one site on either side of the sequences encoding the positive selection marker, sequences encoding a light generating protein, and the promoter. Insertion sites are, for example, restriction endonuclease recognition sites, and can, for example, represent unique restriction sites. In this way, the vector can be digested with the appropriate enzymes and the targeting sequences ligated into the vector.

Optionally, the targeting construct can contain a polynucleotide encoding a negative selection marker. Suitable negative selection markers include, but are not limited to, HSV-tk (see, e.g., Majzoub et al. (1996) *New Engl. J. Med.* 334:904-907 and U.S. Pat. No. 5,464,764), as well as genes encoding various toxins including the diphtheria toxin, the tetanus toxin, the cholera toxin and the pertussis toxin. A further negative selection marker gene is the hypoxanthine-guanine phosphoribosyl transferase (HPRT) gene for negative selection in 6-thioguanine.

Exemplary promoters to be associated with the sequences encoding a light generating protein have been described above.

Central to this aspect of the present invention is the fact that the targeting constructs contain Atargeting@ sequences (flanking the light generating protein-encoding sequence and promoter) derived from a single-copy, non-essential gene. These targeting sequences in the construct act via homologous recombination to replace at least a portion of the non-essential gene in the genome with the light-generating protein-encoding sequences (e.g., luciferase) operably linked to a selected promoter.

Non-limiting examples of targeting sequences for use in generating transgenic mice include sequences obtained from or derived from vitronectin, Fos B and galactin 3. A search of Mouse Knockout & Mutation Database (Genome Systems, Inc., St. Louis, Mo.) can be used to identify genes that have been knocked-out in mice where the generated knockout mice displayed no obvious defects.

Some preferred single-copy, non-essential genes with no phenotypes of the present invention include, but are not limited to, the following: Moesin (Msn), Doi Y., et al., J Biol Chem 1999, 274:2315B2321; Plasminogen activator inhibitor, type II (Planh2) and Planh1, Dougherty K. M., Proc Natl Acad Sci USA 1999, 96:686B691; Nuclear receptor coactivator 1 (Ncoa1), Qi C, et al. (1999) Proc Natl Acad Sci USA 96:1585B1590; Nuclear factor of kappa light chain gene enhancer in B-cells inhibitor, alpha and beta (Nfkbia and Nfkbib), Cheng J D, et al. (1998) J Exp Med 6:1055B1062; H19 fetal liver mRNA (H19), Jones B K, et al. (1998) Genes Dev 12:2200B2207; Prion protein (Prnp), Lipp HP, et al. Behav Brain Res 1998, 95:47B54; Centromere autoantigen B (Cenpb), Perez-Castro AV, et al. Dev Biol 1998, 201:135B143; Placentae and embryos oncofetal gene (Pem), Pitman J L, et al. Dev Biol 1998, 202:196B214; Externally regulated phosphatase (Ptpn16), Dorfman K, et al. Oncogene 1996, 13:925B931; Transformation related protein 53 (Trp53), Ohashi M, et al. Jpn J Cancer Res 1996, 87:696B701; H1-0 histone (H1fv), Sirotkin A M, et al. Proc Natl Acad Sci U S A 1995, 92:6434B6438; Creatine kinase, mitochondrial 1, ubiquitous (Ckmt1), Steeghs K, et al. Biochim Biophys Acta 1995, 1230:130B 138; Neuroblastoma ras oncogene (Nras), Umanoff H, et al. Proc Natl Acad Sci USA 1995, 92:1709B1713; Vitronectin (Vtn), Zheng X, et al. Proc Natl Acad Sci U S A 1995, 92:12426B12430; Vimentin (Vim), Colucci G E, et al. Cell 1994, 79:679B694; Cellular retinoic acid binding protein I (Crabpl), Gorry P, et al. Proc Natl Acad Sci USA 1994, 91:9032B9036; Retinoic acid receptor beta2 (RARbeta2), Mendelsohn C, et al. Dev Biol 1994, 166:246B258; Retinoic acid receptor, alpha (Rara), Li E, et al. Proc Natl Acad Sci USA 1993, 90:1590B1594, Lufkin T, et al. Proc Natl Acad Sci USA 1993, 90:7225B7229; Lectin, galactose binding, soluble 1 (Lgals1), Poirier F, Robertson E J. Development 1993, 119: 1229B1236; Myogenic differentiation 1 (Myod1), Rudnicki M A, et al. Cell 1992, 71:383B390; and Tenascin C (Tnc), Saga Y, et al. Genes Dev 1992, 6:1821B1831. In view of the guidance of the present specification, one of ordinary skill in the art can select similar, suitable, single-copy, non-essential genes in mice and other cell types/organisms.

The targeting constructs containing the expression cassettes of the present invention, wherein the expression cassette is flanked by sequences obtained from the gene into which integration via homologous recombination is being targeted, are introduced into a pluripotent cell (e.g., E S cell, Robertson, E. J., In: Current Communications in Molecular Biology, Capecchi, M. R. (ed.), Cold Spring Harbor Press, Cold Spring Harbor, N.Y. (1989), pp. 39-44). Suitable ES cells may be derived or isolated from any species or from any strain of a particular species. Although not required, the pluripotent cells are typically derived from the same species as the intended recipient. ES cells may be obtained from commercial sources, from International Depositories (e.g., the ATCC) or, alternatively, may be obtained as described in Robertson, E. J., supra. Examples of clonally-derived ES cells lines include 129/SVJ ES cells, RW-4 and C57BL/6 ES cells (Genome Systems, Inc.).

ES cells are cultured under suitable conditions, for example, as described in Ausubel et al., section 9.16, supra. Preferably, ES cells are cultured on stomal cells (such as STO cells (especially SNC4 STO cells) and/or primary embryonic fibroblast cells) as described by E. J. Robertson, supra, pp 71-112. Culture media preferably includes leukocyte inhibitory factor ("lif") (Gough, N. M. et al., Reprod. Fertil. Dev. 1:281-288 (1989); Yamamori, Y. et al., Science 246:1412-1416 (1989), which appears to help keep the ES cells from differentiating in culture. Stomal cells transformed with the gene encoding lif can also be used.

The targeting constructs are introduced into the ES cells by any method which will permit the introduced molecule to undergo recombination at its regions of homology, for example, micro-injection, calcium phosphate transformation, or electroporation (Toneguzzo, F. et al., Nucleic Acids Res. 16:5515-5532 (1988); Quillet, A. et al., J. Immunol. 141:17-20 (1988); Machy, P. et al., Proc. Natl. Acad, Sci. (U.S.A.) 85:8027-8031 (1988)). The construct to be inserted into the ES cell must first be in the linear form. Thus, if the knockout construct has been inserted into a vector as described above, linearization is accomplished by digesting the DNA with a suitable restriction endonuclease selected to cut only within the vector sequence and not within the knockout construct sequence. If the ES cells are to be electroporated to insert the construct, the ES cells and construct DNA are exposed to an electric pulse using an electroporation machine and following the manufacturer's guidelines for use. After electroporation, the ES cells are typically allowed to recover under suitable incubation conditions. The cells are then cultured under conventional conditions, as are known in the art, and screened for the presence of the construct.

Screening and selection of those cells into which the targeting construct has been integrated can be achieved using the positive selection marker and/or the negative selection marker in the construct. In preferred embodiments, the construct contains both positive and negative selection markers. In one aspect, methods which rely on expression of the selection marker are used, for example, by adding the appropriate substrate to select only those cells which express the product of the positive selection marker or to eliminate those cells expressing the negative selection marker. For example, where the positive selection marker encodes neomycin resistance, G418 is added to the transformed ES cell culture media at increasing dosages. Similarly, where the negative selection marker is used, a suitable substrate (e.g., gancyclovir if the negative selection marker encodes HSV-TK) is added to the cell culture. Either before or after selection using the appropriate substrate, the presence of the positive and/or negative selection markers in a recipient cell can also be determined by others methods, for example, hybridization, detection of radiolabelled nucleotides, PCR and the like. In preferred embodiments, cells having integrated targeting constructs are first selected by adding the appropriate substrate for the positive and/or negative selection markers. Cells that survive the selection process are then screened by other methods, such as PCR or Southern blotting, for the presence of integrated sequences.

After suitable ES cells containing the construct in the proper location have been identified, the cells can be inserted into an embryo, preferably a blastocyst. The blastocyts are obtained by perfusing the uterus of pregnant females. In one embodiment, the blastocyts are obtained from, for example, the FVB/N strain of mice and the ES cells are obtained from, for example, the C57BL/6 strain of mice. Suitable methods for accomplishing this are known to the skilled artisan, and are set forth by, e.g., Bradley et al., (1992) Biotechnology, 10:534-539. Insertion into the embryo may be accomplished in a variety of ways known to the skilled artisan, however a preferred method is by microinjection. For microinjection, about 10-30 ES cells are collected into a micropipet and injected into embryos that are at the proper stage of development to permit integration of the foreign ES cell containing the construct into the developing embryo. The suitable stage of development for the embryo used for insertion of ES cells is species dependent, in mice it is about 3.5 days.

While any embryo of the right stage of development is suitable for use, it is preferred that blastocysts are used. In addition, preferred blastocysts are male and, furthermore, preferably have genes encoding a coat color that is different from that encoded by the genes ES cells. In this way, the offspring can be screened easily for the presence of the knockout construct by looking for mosaic coat color (indicating that the ES cell was incorporated into the developing embryo). Thus, for example, if the ES cell line carries the genes for black fur, the blastocyst selected will carry genes for white or brown fur.

After the ES cell has been introduced into the blastocyst, the blastocyst is typically implanted into the uterus of a pseudopregnant foster mother for gestation. Pseudopregnant females are prepared by mating with vasectomized males of the same species and successful implantation usually must occur within about 2-3 days of mating.

Offspring are screened initially for mosaic coat color where the coat color selection strategy has been employed. Southern blots and/or PCR may also be used to determine the presence of the sequences of interest. Mosaic (chimeric) offspring are then bred to each other to generate homozygous animals. Homozygotes and heterozygotes may be identified by Southern blotting of equivalent amounts of genomic DNA from mice that are the product of this cross, as well as mice that are known heterozygotes and wild type mice. Alternatively, Northern blots can be used to probe the mRNA to identify the presence or absence of transcripts encoding either the replaced gene, the sequences encoding the light generating protein (e.g., luciferase gene), or both. In addition, Western blots can be used to assess the level of expression of the luciferase protein with an antibody against the luciferase gene product. Finally, in situ analysis (such as fixing the cells and labeling with antibody) and/or FACS (fluorescence activated cell sorting) analysis of various cells from the offspring can be conducted using suitable (e.g., anti-luciferase) antibodies to look for the presence or absence of the targeting construct.

In one embodiment of the present invention, the animals are from the C57BL/6 mouse strain. This strain develops a variety of tumors and has been used to develop a number of tumor cells lines, for example, B16 melanoma cells (including, B16F10, B16D5, and B16F1), Lewis lung carcinoma cells (including, LLC, LLC-h59), T241 mouse fibrosarcoma cells, RM-1 and pTC2 mouse prostate cancer cells, and MCA207 mouse sarcoma cells. These cell lines have been extensively used for in vivo tumor biology studies after injection into C57BL/6 mice. The generated targeted transgenic mice in the Examples are in C57BL/6 genetic background and these animals are suitable for injection or implantation of such tumor cells, as well as other tumor cells described in literature that are immunocompatent for C57BL/6 mice. Thus, the transgenic animals can then be used, for example, to monitor, in vivo, tumor progression (e.g., growth) and the efficacy of therapies on tumor regression. For example, where the transgenic animal is tumor-susceptible, it is monitored for expression of a reporter, e.g., luciferase, which is indicative of tumorigenesis and/or angiogenesis. The monitoring of expression of luciferase reporter expression cassettes using non-invasive whole animal imaging has been described (Contag, C. et al, U.S. Pat. No. 5,650,135, Jul. 22, 1997, herein incorporated by reference; Contag, P., et al, *Nature Medicine* 4(2):245-247, 1998; Contag, C., et al, OSA TOPS on *Bio-* medical *Optical Spectroscopy and Diagnostics* 3:220-224, 1996; Contag, C. H., et al, *Photochemistry and Photobiology* 66(4):523-531, 1997; Contag, C. H., et al, *Molecular Microbiology* 18(4):593-603, 1995). Such imaging typically uses at least one photo detector device element, for example, a charge-coupled device (CCD) camera.

The transgenic animals described herein can also be used to determine the effect of an analyte (e.g., therapy), for example on tumor progression where the promoter induces light generating protein expression when a tumor develops. Methods of administration of the analyte include, but are not limited to, injection (subcutaneously, epidermally, intradermally), intramucosal (such as nasal, rectal and vaginal), intraperitoneal, intravenous, oral or intramuscular. Other modes of administration include oral and pulmonary administration, suppositories, and transdermal applications. Dosage treatment may be a single dose schedule or a multiple dose schedule. For example, the analyte of interest can be administered over a range of concentration to determine a dose/response curve. The analyte may be administered to a series of test animals or to a single test animal (given that response to the analyte can be cleared from the transgenic animal).

Breeding of the chimeric mice generates homozygous targeted transgenic mice, as depicted in FIG. 1. The targeted mice are used to monitor gene expression through the measurement of luciferase mediated light emission from the mice. In a preferred embodiment, the targeted mouse has a light coat color (e.g., white coat color), because the black colored coat (an example of a dark coat color) of C57BL/6 mice can absorb light emitted from the body and may interfere the sensitivity of the bioluminescence assay. An inbred mouse strain C57BL/6-Tyr C2j/+strain (Jackson Laboratory, Bar Harbor, Minn.) is available for this purpose. This strain of mice have white color coat, yet they still have the same genetic background as C57BL/6 mice except that the gene responsible for the black coat color is mutated. Accordingly, this strain may provide useful breeding partners. Unfortunately, C57BL/6-Tyr C2j/+ES cells are not currently available. Therefore, the designed breeding program illustrated in FIG. 1 is aimed to generate mice that are homozygous for the target transgene and have white coat color. C57BL/6 ES cells are prepared as described above and introduced into a suitable blastocyst (e.g., from the FVB/N strain of mice). The blastocysts are implanted into a foster mother. Chimeric mice are shown in FIG. 1 as white animals with black and green patches. Chimeric animals are bred with C57BL/6-Tyr C2j/+mice to create F1 hybrids. Subsequent breeding of the F1 hybrids generates several type of mice, including the one that is homozygous for the target transgene and has a white coat color (shown in FIG. 1 as b/b; L/L), which is used for in vivo gene regulation monitoring.

A C57BL/6 mouse and a C57BL/6-Tyr C2j/+mouse are considered to be substantially isogenic. Accordingly, the method of the present invention exemplified in FIG. 1 provides a means for generating cohorts or breeding groups of substantially isogenic mice in a selected genetic background carrying at least one transgene of interest. Having substantially isogenic transgenic mice comprising a cohort for use in the methods of the present invention allows for reduction of error based that originates in genetic background variations.

Transgenic animals of the present invention carrying more than one reporter expression cassette may be created directly by the above-described methods (e.g., multiple expression cassettes can be integrated at a single site, or individual expression cassettes can be integrated, each at a different site). Alternatively, such animals may be created by breeding a first transgenic animal carrying at least one reporter expression cassette by a second transgenic animal carrying at least one reporter expression cassette.

4.2.0 Imaging

Non-invasive imaging and/or detecting of light-emitting conjugates in mammalian subjects was described in co-owned U.S. Pat. No. 5,650,135, by Contag, et al., issued Jul. 22, 1997, and herein incorporated by reference.

In the imaging method, the conjugates contain a biocompatible entity and a light-generating moiety. Biocompatible entities include, but are not limited to, small molecules such as cyclic organic molecules; macromolecules such as proteins; microorganisms such as viruses, bacteria, yeast and fungi; eukaryotic cells; all types of pathogens and pathogenic substances; and particles such as beads and liposomes. In another aspect, biocompatible entities may be all or some of the cells that constitute the mammalian subject being imaged.

Light-emitting capability is conferred on the biocompatible entities by the conjugation of a light-generating moiety. Such moieties include fluorescent molecules, fluorescent proteins, enzymatic reactions giving off photons and luminescent substances, such as bioluminescent proteins. The conjugation may involve a chemical coupling step, genetic engineering of a fusion protein, or the transformation of a cell, microorganism or animal to express a bioluminescent protein.

For example, in the practice of the present invention, the biocompatible entities are the cells constituting the mammalian subject being imaged. In this case, the light-generating moiety is typically a bioluminescent or fluorescent protein "conjugated" to the cells through localized, promoter-controlled expression from a vector construct introduced into the cells by having made a transgenic or chimeric animal.

Light-emitting conjugates are typically administered to a subject by any of a variety of methods, allowed to localize within the subject, and imaged. Since the imaging, or measuring photon emission from the subject, may last up to tens of minutes, the subject is usually, but not always, immobilized during the imaging process.

Imaging of the light-emitting entities involves the use of a photo detector capable of detecting extremely low levels of light—typically single photon events—and integrating photon emission until an image can be constructed. Examples of such sensitive photo detectors include devices that intensify the single photon events before the events are detected by a camera, and cameras (cooled, for example, with liquid nitrogen) that are capable of detecting single photons over the background noise inherent in a detection system.

Once a photon emission image is generated, it is typically superimposed on a "normal" reflected light image of the subject to provide a frame of reference for the source of the emitted photons (i.e. localize the light-emitting conjugates with respect to the subject). Such a "composite" image is then analyzed to determine the location and/or level of expression of a reporter gene in the subject.

5.0.0 Utility

There are several rate-limiting steps that can interfere with the progression from drug discovery to drug development. Biological assessment in predictive animal models is one of these rate-limiting steps and it is among the most difficult problems faced by the pharmaceutical industry. The enormous amount of time and money needed to develop new drugs can largely be attributed to this problem.

Drug development is expensive because it is inefficient. Despite the enormous effort dedicated to improving the predictive value of in vitro screening and other high-throughput technologies most new chemical entities fail in pre-clinical/ clinical testing. Moreover, the vast majority of compounds that proceed to Phase III clinical trials ultimately fail.

Experiments performed in support of the present invention suggested that a solution to this problem is the development of drug screening technology that is carried out in vivo. The test animals and compound screening methods of the present invention allow toxicological screening of compounds and the collection of relevant real-time data in living animals providing the ability to obtain superior data on a selected compound (analytes) toxicity before proceeding to pre-clinical or clinical trials. Data obtained using the test animals and methods of the present invention will improve the efficiency of the drug development process by allowing the selection of the least toxic candidates (i.e., the candidates having the fewest undesirable side effects) for continued development.

The test animals and methods of the present invention provide an in vivo differential display technology that may allow high-throughput screening of compounds in living animals. By performing screening of candidate compounds in living animals more physiological and pharmacological data can be compiled than could possible be done in vitro. For example, by using an animal or series of animals containing reporter gene expression cassettes of the present invention the toxicity of a test analyte can be determined relative to a wide variety of stressinduced systems in the live animal including, but not limited to, DNA-related stress, proteinrelated stress, energy/ionic-related stress, redox-related stress, cell surface receptor-mediated stresses, cellular energy related stress. Further, effects of such compounds (or test analytes) on identified target pathways (e.g., biochemical, developmental, oncogenic, see above) can be effectively evaluated in live animals. Accordingly, a great deal of information can be compiled concerning the specific nature of, for example, toxic or undesirable side effects of a test compound/analyte using the test animals and methods of the present invention.

By evaluating test compounds/analytes in vivo more accurate assessments can be obtaining concerning toxicological (including potential side effects of test substances) and pharmacological information. This information allows more accurate predictions as to how the test compound/analyte will behave in intact mammalian systems.

As is apparent to one of skill in the art, various modification and variations of the above embodiments can be made without departing from the spirit and scope of this invention. These modifications and variations are within the scope of this invention.

What is claimed is:

1. A transgenic mouse comprising a panel of expression cassettes, said transgenic mouse produced by a method comprising the steps of introducing a first expression cassette comprising a first promoter derived from a first stress-inducible gene into a mouse at an embryonic stage, said promoter operably linked to sequences encoding a first light generating polypeptide, and introducing a second expression cassette comprising a second promoter derived from a second stress-inducible gene into said mouse at an embryonic stage, said promoter operably linked to sequences encoding a second light generating polypeptide and said second promoter derived from a different stress-inducible gene than said first promoter.

2. A method of determining the effect of an analyte on gene expression mediated by promoters derived from stress-inducible genes, wherein said expression is in a living transgenic mouse, said method comprising administering the analyte to a living transgenic mouse of claim 1, wherein administering of said analyte is carried out under conditions that permit light generation mediated by said light generating polypeptide in the transgenic mouse, determining the effect of the analyte on expression of the light generating polypeptide in a living transgenic mouse wherein said expression is mediated by at least one of the promoters.

3. The method of claim 2, wherein said conditions that permit light generation mediated by the light generating polypeptide includes administering, to the transgenic mouse, at least one substrate for the light generating polypeptide.

4. A noninvasive method for detecting a level of expression in response to an analyte, wherein said expression is (i) mediated by promoters derived from stress-inducible genes, and (ii) in a living transgenic mouse, said method comprising (a) administering the analyte to a living transgenic mouse of claim 1, wherein administering of said analyte is carried out under conditions that permit light generation mediated by said light generating polypeptide, (b) placing the transgenic mouse within a detection field of a photo detector device, (c) maintaining the transgenic mouse in the detection field of the device, and (d) during said maintaining, measuring photon emission from the transgenic mouse with the photo detector device to detect the level of expression of the light generating polypeptide in the living transgenic mouse wherein said expression is mediated by at least one of the promoters.

5. The method of claim 4, further comprising, (e) repeating steps (b) through (d) at selected intervals, wherein said repeating is effective to detect changes in the level of the light emission in the transgenic mouse over time.

6. A method of providing a transgenic mouse suitable for screening a selected analyte, comprising generating a transgenic mouse of claim 1, and providing said transgenic mouse or progeny thereof for use in screening a selected analyte.

7. The transgenic mouse of claim 1, wherein the method further comprises introducing a third expression cassette comprising a promoter derived from a third stress-inducible gene into a mouse at an embryonic stage, said third promoter operably linked to sequences encoding a third light generating polypeptide and said third promoter derived from a different stress-inducible gene than said first and second promoters.

8. The transgenic mouse of claim 7, wherein (i) said first, second, and third promoters are each derived from a different gene, and (ii) said first, second, and third light generating polypeptides produce the same color of light.

9. The transgenic mouse of claim 7, wherein (i) said first, second, and third promoters are each derived from a different gene, and (ii) at least two of said first, second, and third light generating polypeptides produce different colors of light.

10. The transgenic mouse of claim 7, said panel further comprising additional expression cassettes, wherein each expression cassette comprises a promoter derived from a different stress-inducible gene, said promoter operably linked to sequences encoding a light generating polypeptide.

* * * * *